US011605451B2

(12) United States Patent
Barbosa De Abreu E Sousa

(10) Patent No.: US 11,605,451 B2
(45) Date of Patent: Mar. 14, 2023

(54) MEDICAMENT DISPENSER

(71) Applicant: Armando Miguel Barbosa De Abreu E Sousa, Caldas da Rainha (PT)

(72) Inventor: Armando Miguel Barbosa De Abreu E Sousa, Caldas da Rainha (PT)

( * ) Notice: Subject to any disclaimer, the term of this patent is extended or adjusted under 35 U.S.C. 154(b) by 380 days.

(21) Appl. No.: 16/641,518

(22) PCT Filed: Sep. 14, 2017

(86) PCT No.: PCT/IB2017/055559
§ 371 (c)(1),
(2) Date: Feb. 24, 2020

(87) PCT Pub. No.: WO2019/038580
PCT Pub. Date: Feb. 28, 2019

(65) Prior Publication Data
US 2021/0193283 A1    Jun. 24, 2021

(30) Foreign Application Priority Data
Aug. 25, 2017   (PT) .......................................... 110266

(51) Int. Cl.
G16H 20/13    (2018.01)
A61M 15/00    (2006.01)
G16H 20/17    (2018.01)

(52) U.S. Cl.
CPC ........ *G16H 20/13* (2018.01); *A61M 15/0003* (2014.02); *G16H 20/17* (2018.01); *A61M 2209/045* (2013.01)

(58) Field of Classification Search
CPC ... G16H 20/13; G16H 20/17; A61M 15/0003; A61M 2209/045
(Continued)

(56) References Cited

U.S. PATENT DOCUMENTS 2,758,710 A * 8/1956 Egmont ............. B65D 83/0847
206/532
3,526,317 A * 9/1970 Vanders ................. B65D 75/30
206/217
(Continued)

FOREIGN PATENT DOCUMENTS

EP      1973593 A2    10/2008
EP      1973593 B1 *  4/2013    ............ A61J 7/0038
(Continued)

*Primary Examiner* — Rakesh Kumar
(74) *Attorney, Agent, or Firm* — Nixon Peabody LLP

(57) ABSTRACT

Disclosed is a medicament dispenser (1) for delivering a medicament (9, 53) to a user (2), the medical dispenser (1) comprising one or more internal storages (3, 52) for storing one or more medicaments (9, 53); a dispensing unit (10, 101) configured to access said one or more internal storages (3, 52) and dispense the medicament (9; 53) based on a predefined dispensing protocol (18); a control unit (13) comprising a user recognition unit (12, 19), adapted to collect user authentication data (76); and a communication module (14), configured to send/receive said user authentication data (76) and a delivery control data (16) associated to said predefined dispensing protocol (18) to/from a remote server (15); wherein said control unit 5 (13) is configured to enable/disable said dispensing unit (10, 101) based on said user authentication data (76) and said delivery control data (16). Also disclosed is a medicament re-filling apparatus (32) for the use with a medicament dispenser (1) upon authentication and validation of its user (2) condition.

6 Claims, 21 Drawing Sheets

(58) Field of Classification Search
USPC ...... 364/479, 413.02, 413.04, 413.03, 513.5; 700/242; 221/2, 9, 15, 197, 82, 7
See application file for complete search history.

(56) References Cited

U.S. PATENT DOCUMENTS

| | | | | |
|---|---|---|---|---|
| 4,223,801 A | * | 9/1980 | Carlson | A61J 7/0472 206/533 |
| 4,695,954 A | * | 9/1987 | Rose | G07F 17/0092 221/9 |
| 4,725,997 A | * | 2/1988 | Urquhart | A61J 7/0436 368/10 |
| 4,767,022 A | * | 8/1988 | Oldorf | G07F 11/18 221/92 |
| 4,798,309 A | * | 1/1989 | Stone | A61J 7/0481 221/15 |
| 4,911,327 A | * | 3/1990 | Shepherd | A61J 7/0481 221/3 |
| 4,975,295 A | * | 12/1990 | Sierra | A23F 5/385 426/594 |
| 5,057,305 A | * | 10/1991 | Aberg | A61K 8/02 424/44 |
| 5,291,191 A | * | 3/1994 | Moore | A61J 7/0445 340/5.91 |
| 5,329,459 A | * | 7/1994 | Kaufman | A61B 5/4833 221/9 |
| 5,392,952 A | * | 2/1995 | Bowden | A61J 7/0481 221/76 |
| 5,587,277 A | * | 12/1996 | Yamashita | G03C 5/265 430/458 |
| 5,646,912 A | * | 7/1997 | Cousin | G06V 20/66 221/96 |
| 5,945,651 A | * | 8/1999 | Chorosinski | A61J 1/035 235/375 |
| 6,087,548 A | * | 7/2000 | Levy | A61M 5/3205 422/26 |
| 6,259,654 B1 | * | 7/2001 | de la Huerga | A61J 7/0481 368/10 |
| 6,332,100 B1 | * | 12/2001 | Sahai | G16H 20/13 700/242 |
| 6,439,422 B1 | * | 8/2002 | Papp | A61J 7/0084 221/13 |
| 7,344,047 B2 | * | 3/2008 | Gilmore | G07F 17/0092 221/13 |
| 7,896,192 B2 | * | 3/2011 | Conley | G07F 17/0092 221/92 |
| 8,112,175 B2 | * | 2/2012 | Handfield | A61J 7/0084 700/242 |
| 8,326,455 B2 | * | 12/2012 | Dunn | G07F 9/02 221/211 |
| 8,364,504 B1 | * | 1/2013 | Bleser | G16H 20/10 705/2 |
| 8,490,795 B2 | * | 7/2013 | Ziemba | B65B 53/02 215/231 |
| 9,836,583 B2 | * | 12/2017 | Garcia | G16H 20/13 |
| 9,974,713 B1 | * | 5/2018 | Song | A61J 7/0445 |
| 10,596,071 B1 | * | 3/2020 | Song | A61J 1/03 |
| 2004/0074917 A1 | * | 4/2004 | McHutchinson | B65D 83/0463 221/302 |
| 2008/0251530 A1 | * | 10/2008 | Holloway | A61J 7/0076 700/231 |
| 2009/0006126 A1 | * | 1/2009 | Champigny | G16H 20/10 705/2 |
| 2009/0105876 A1 | * | 4/2009 | Simpson | G07F 9/026 700/242 |
| 2009/0167531 A1 | * | 7/2009 | Ferguson | G16H 40/67 340/572.1 |
| 2009/0281657 A1 | * | 11/2009 | Gak | G07F 17/0092 700/242 |
| 2010/0100237 A1 | * | 4/2010 | Ratnakar | A61J 7/0418 221/97 |
| 2011/0202174 A1 | * | 8/2011 | Bogash | G07F 9/026 700/242 |
| 2011/0226817 A1 | * | 9/2011 | Ortenzi | A61J 1/18 222/424.5 |
| 2013/0222116 A1 | * | 8/2013 | Barry, III | G16H 40/20 340/10.1 |
| 2013/0226339 A1 | * | 8/2013 | Ervin | G16H 20/13 700/240 |
| 2013/0238119 A1 | * | 9/2013 | Simmons | A61J 7/0481 700/237 |
| 2014/0214200 A1 | * | 7/2014 | Chrusciel | A61J 7/0076 221/15 |
| 2014/0278510 A1 | * | 9/2014 | McLean | G16H 20/13 705/2 |
| 2014/0297028 A1 | * | 10/2014 | Bilotti | A61J 7/0472 700/237 |
| 2014/0309772 A1 | * | 10/2014 | Shen | G16H 20/13 700/237 |
| 2015/0359711 A1 | * | 12/2015 | Ducatt | G16Z 99/00 221/13 |
| 2016/0158107 A1 | * | 6/2016 | Dvorak | A61J 7/0084 221/9 |
| 2016/0207691 A1 | * | 7/2016 | Benouali | B65D 51/30 |
| 2016/0283691 A1 | * | 9/2016 | Ali | G16H 20/13 |
| 2016/0300031 A1 | * | 10/2016 | Salwan | G06F 16/9535 |
| 2017/0079887 A1 | * | 3/2017 | Song | A61J 1/03 |
| 2017/0242976 A1 | * | 8/2017 | Howieson | A61J 7/04 |
| 2018/0028406 A1 | * | 2/2018 | Patton | A61J 7/0069 |
| 2018/0286506 A1 | * | 10/2018 | Farhat | G06Q 20/085 |
| 2019/0267123 A1 | * | 8/2019 | Stueckemann | G06Q 30/06 |
| 2020/0179230 A1 | * | 6/2020 | Molloy | A61J 7/0436 |
| 2020/0234811 A1 | * | 7/2020 | Greenspan | A61J 7/0418 |
| 2021/0193283 A1 | * | 6/2021 | Barbosa De Abreu E Sousa | A61J 7/0418 |
| 2021/0264716 A1 | * | 8/2021 | Norbeck | G07F 11/58 |

FOREIGN PATENT DOCUMENTS

| | | | | | |
|---|---|---|---|---|---|
| WO | WO-2008089249 A1 | * | 7/2008 | ......... | G06F 19/3456 |
| WO | WO-2016130109 A1 | * | 8/2016 | ............ | A61J 7/0418 |
| WO | WO-2017027974 A1 | * | 2/2017 | ............ | G06Q 50/22 |
| WO | 2016130109 A1 | | 8/2018 | | |

* cited by examiner

MEDICAMENT DISPENSER

The present invention relates to a medicament dispenser for delivering a medicament to a user.

BACKGROUND OF THE INVENTION

In medicine there is often the need to control and/or monitor correct intake of medication, such as drugs and medicine which are typically prescribed for conditions concerning the nervous system, especially the brain, peripheral nerves, and spinal cord, due to a broad scope of medical situations. Within this scope there are drugs and medicine described and listed by FDA (United States Food and Drug Administration) as Neurology Drugs and Nervous System Drugs, including medication for pain relief purposes, such as opioids, and for which there is the need of rigorous control and monitoring of related effects. Concerning medicines for pain relief purposes, like opioids, those will be referred in this document their four subcategories: opiates, semi-synthetic opioids, synthetic opioids, and endogenous opioids.

Drugs and medicine described above may have a large spectrum of applications for different types of patients' conditions concerning, but not only, post-surgery, cancer treatments, as well as brain and nervous system conditions such as: Alzheimer's Disease, Attention Deficit Hyperactivity Disorder (ADHD), Carpal Tunnel Syndrome, Huntington's Disease, dementia, memory loss, multiple sclerosis, muscular dystrophy, Parkinson's Disease, Tourette's Syndrome, and others, which they all require to careful follow related prescription and its effects.

FDA list of approved drugs for neurology and the nervous system includes a plurality of types of such medication supposed to be prescribed to patients by their medical doctors, as such medicines are considered "prescription drugs" or "prescription strong medicines", which include:

Opioids, as Opiate pain relievers, such as methadone, morphine, oxycodone (OxyContin), fentanyl, sufentanil, levorphanol, oxymorphone, hydromorphone, meperidine (Demerol), and tramadol, as well as any chemical variation or combination of those;

Medicines that can be prescribed to be used with opiate pain relievers. Such medicines are usually prescribed to help pain medicine performance treating patient's symptoms, or they are specifically prescribed for certain types of pain. These medicines include, but not only: Bisphosphonates (e.g. dexamethasone, and prednisone), Anti-inflammatory drugs and corticosteroids, local anesthetics (e.g. lidocaine, and capsaicin, to help pain in skin and surround tissues), Anticonvulsants, Antidepressants, and other medicines aiming to have similar effects.

The medicines described above are given to patients in several ways depending of the specific conditions of each patient, and in general they are given by mouth. Although, in several circumstances, for example when the patient may have difficulties, or related problems, in swallowing capsules, these types of medicines may be taken in several other ways, including in cases when faster pain relief is needed.

In general, there are the following common ways of taking these medicines:

a) By mouth: such as pills, capsules, tablets, liquids, and medicines that dissolve on the tongue or under the tongue, as well as through aerosol to be absorbed via the mouth and respiratory system into the body;

b) Using skin patches: the patch has medicine incorporated that is absorbed into the body through the skin;

c) With rectal suppositories: such as in pills, or capsules, which are put inside the rectum and absorbed into the body;

d) With needles: such as injections, or into a vein (IV—intravenous). A patient taking medicines via IV may be able to use a Patient Controlled Analgesia (PCA) pump, which lets the patient control pain medicines in some limited ways;

e) With infusion pumps, as pain relief pumps: which are placed under the skin of the patients to deliver pain medicine directly to their spine;

f) Into the spine: when medicine is put into the area around the spinal cord, such as with epidural or spinal anesthesia.

Taking into consideration that the ways d), e) and f) require support from third parties, namely certified health professionals or others equivalent, for the first set-up as well as for further control and monitoring, ways a), b) and c) are manners commonly used when patients have conditions of total or partial autonomy.

Due to the specificity of these types of medicines there are potential problems and risks to the patients that are associated to hazardous situations of its misuse, including those of not following defined medical prescription, and which may occur by the following main failure modes:

Lack of self-control of the patient on the frequency and/or quantity of intake of the specific medicine or pharma product containing opioids to be administrated according medical prescription;

Deliberately wrong intake by the patient of the specific medicine or pharma product containing opioids, out of the quantity and/or frequency as medically prescribed;

Unconscious intake, or deliberately conscious intake, by individuals which are not the intended patient and user of the specific medicine or pharma product according medical prescription.

Such main failure modes described above can directly, or indirectly, cause situations that may put in danger the life of individuals that take the medicines or pharma product containing opioids, as well as it may put in danger the life of other individuals that may directly, or indirectly, be affected by any conscious, or unconscious, action of misconduct in any circumstances of such person, including wrong action, or lack of action, on professional duty. These are problems that manufacturers and medical authorities that prescribe related medicines or pharma products, or devices that deliver such products currently on the market, could not yet solve in a robust and reliable way, and accidental intakes of such products keep often occurring in an increasing and alarming way, as published statistics by governmental and independent health authorities show. Just referring to U.S.A., according to governmental official data of Centers for Disease Control and Prevention, "overdose deaths involving prescription opioids have quadrupled since 1999, and so have sales of these prescription drugs. From 1999 to 2015, more than 183,000 people have died in the U.S.A. from overdoses related to prescription opioids, in 2014 around 2 million Americans abused or were dependent on prescription opioids, and every day, over 1,000 people are treated in hospital emergency departments for misusing prescription opioids".

The main failure modes leading to related to prescription strong medicines also apply to any other medicine drugs or pharma products, with strong effect in human body for specific medical purposes which are mostly taken by mouth, such as pills, capsules, tablets, liquids, or aerosols, and which require proper control and compliance with the prescribed doses and intake scheduling.

As explained, due to several reasons, including social and cultural factors, the intake of the several types of medicines described above is often not compliant to the prescription, resulting in serious health problems to those affected, including death, and every year thousands of such cases are reported by national health authorities worldwide. This reality affects mostly developed countries, in particular United States of America, Canada, European Union, Japan, and other countries, also following a worldwide trend of increasing elder population, and related consumption of prescribed pain relievers medicines.

SUMMARY

Purpose of the present invention is to overcome the above-mentioned drawbacks by providing a medicament dispenser as substantially defined herein.

Further object of the present invention is to provide an auxiliary device as substantially herein.

Further object of the present invention is to provide a medicament re-filling apparatus as substantially defined herein.

Further objects of the present invention is to provide an inhaler as substantially defined herein.

Further object of the present invention is to provide a medical system as substantially defined herein.

Further preferred characteristics are defined in the corresponding dependent claims.

According to a first aspect of the present invention, it is provided a medical dispenser for delivering a medicament to a user, the medical dispenser comprising:
 one or more internal storages for storing one or more medicaments;
 a dispensing unit configured to access the one or more internal storages and dispense the medicament based on a predefined dispensing protocol;
 a control unit comprising:
 a user recognition unit adapted to collect user authentication data; and
 a communication module, configured to send/receive user authentication data and delivery control data associated to said predefined dispensing protocol to/from a remote server;
wherein the control unit is configured to enable/disable the dispensing unit based on user authentication data and delivery control data.

In an exemplary embodiment, the communication module is configured to send/receive the delivery control data and the user authentication data through wireless means.

In an exemplary embodiment, the control unit is further configured to collect health data associated to the user.

In an exemplary embodiment, the communication module is further configured to send/receive the health data to/from the remote server, the delivery control data being adjusted based on the user health data.

In an exemplary embodiment, the communication module is configured such to send/receive the health data through wireless means.

In an exemplary embodiment, the medicament dispenser comprises a camera for detecting user's visual data associated to user's physical characteristics, the control unit being configured to process the visual data such to obtain the health data. The camera can also be used to timely perform pupilometry and correlate with the effects of medicine intake.

In an exemplary embodiment, the control unit is configured to receive/send health data associated to the user from/to an auxiliary external device.

In an exemplary embodiment, the internal storage is an elongate compartment having a top end and a bottom end, the elongate compartment being adapted to accommodate a plurality of medicaments in the form of a pile.

In an exemplary embodiment, the dispensing unit comprises an ejector configured to slide along a transversal direction R with respect to an axis A of the elongate compartment, the ejector being slidable from an inner position where it collects a medicament located at the bottom end of the compartment to an outer position where the ejector protrudes out of the dispenser to deliver the medicament and vice/versa.

In an exemplary embodiment, the medicament dispenser comprises a resilient means located at the top end of the compartment, the resilient means being arranged to exert a pressure on the pile such to ensure that the medicament located at the bottom end of the compartment is intercepted by the ejector for delivery when the latter is in the inner position.

In an exemplary embodiment, the medicament dispenser further comprises a blocking device associated to the ejector, the blocking device being adapted to prevent/allow a movement of the ejector when activated/de-activated by the control unit.

In an exemplary embodiment, the activation/de-activation of the blocking system is operated by the control unit based on the user authentication data and the delivery control data In an exemplary embodiment, the activation/de-activation of the blocking system is operated by the control unit based on the health data.

In an exemplary embodiment, the ejector is connected to a slidable button located on an external wall of the medicament dispenser, the slidable button being operable by the user.

In an exemplary embodiment, the internal storage is configured to accommodate a canister that is adapted to store the medicament in a form such to be delivered as an inhalable aerosol.

In an exemplary embodiment, the dispensing unit comprises a movable shutter for allowing/preventing access to the canister.

In an exemplary embodiment, the movable shutter is connected to a slidable lever of the medicament dispenser and operable by the user.

In an exemplary embodiment, the canister comprises an upper component adapted to be connected to an inhaler, for inhaling the aerosol.

In an exemplary embodiment, the medicament dispenser comprises a cover for accessing the internal storage, wherein the cover is removably connected to a main body of the medicament dispenser by a locking/unlocking means.

In an exemplary embodiment, the locking/unlocking means is configured to cooperate for connecting/removing the cover with an external medicament re-filling apparatus, when the latter is located in physical proximity with the medicament dispenser.

In an exemplary embodiment, the medicament dispenser further comprises a safety clamping mechanism configured to irreversibly prevent unlocking of the cover.

In an exemplary embodiment, the safety clamping mechanism is activable by the control unit upon reception of a service termination order from the remote server.

In an exemplary embodiment, the safety clamping mechanism is associated to an internal electric circuit arranged to detect a local attempt of forcing the medicament dispenser to access the internal storage, wherein the safety clamping system is activated if such attempt is detected.

In an exemplary embodiment, the safety clamping mechanism comprises an electro-mechanical switch including a component having a slidable pin, the pin being arranged when activated to project into a receiving groove of the cover to prevent its removal.

In an exemplary embodiment, the medicament dispenser further comprises a destruction system of the medicaments.

In an exemplary embodiment, the destruction system is activable by the control unit upon reception of a service destruction order from the remote server.

In an exemplary embodiment, the destruction system is associated to an internal electric circuit arranged to detect a local attempt of forcing the medicament dispenser to access the internal storage, wherein the destruction system is activated if such attempt is detected.

In an exemplary embodiment, the destruction system comprises a reservoir disposed within the internal storage, the reservoir having frangible walls and containing a medicament-neutralizing agent.

In an exemplary embodiment, the medicament dispenser may comprise a puncher element configured to break, when activated, the frangible walls, wherein the reservoir is arranged within the internal storage such that upon breakage of the frangible walls the medicament-neutralizing agent is released within the internal storage.

In an exemplary embodiment, the destruction system comprises an electro-mechanical switch including a component having a slidable pin such that, when activated, the slide of the pin triggers a release of the puncher element for breaking the reservoir walls.

In an exemplary embodiment, the electro-mechanical switch is arranged such that the slide of the pin causes both its projection into the receiving groove of the cover for preventing its removal and the release of the puncher element for breaking the reservoir walls.

According to a further aspect of the present invention, it is provided a medicament dispenser for delivering a medicament to a user, comprising:
- a connector for connecting the medicament dispenser to an external storage adapted to store a medicament;
- a control unit comprising:
  - a user recognition unit adapted to collect user authentication data; and
  - a communication module, configured to send/receive said user authentication data and a delivery control data to/from a remote server, the delivery control data being associated to a predefined dispensing protocol of the user;

wherein the control unit is configured to enable/disable delivery of medicament from the external storage to the user based on the user authentication data and the delivery control data.

A further aspect of the present invention provides an auxiliary device for use with the medicament dispenser for monitoring health of a user, the auxiliary device being configured to collect health data of the user and to send/receive the health data to the medicament dispenser.

In an exemplary embodiment, the auxiliary device is a wearable device.

A further aspect of the present invention provides an inhaler for use with the medicament dispenser.

A further aspect of the present invention provides a medicament re-filling apparatus for use with the medicament dispenser.

In an exemplary embodiment, the medicament re-filling apparatus comprises a communication system configured to exchange validation data with the control unit of the medicament dispenser and/or a remote server for authenticating the medicament dispenser.

In an exemplary embodiment, the medicament re-filling apparatus comprises a base with a receiving slot for internally receiving at least a portion of the medicament dispenser.

In an exemplary embodiment, the communication system is configured to exchange validation data with the control unit and/or the remote server through wireless means.

A further aspect of the present invention provides medical system for a medicament intake and monitoring, comprising the medicament dispenser and the auxiliary device.

BRIEF DESCRIPTION OF THE DRAWINGS

Still further advantages, as well as features and ways of carrying out the present invention will become apparent from the following detailed description of a preferred embodiment, presented by way of a non-limiting example, making reference to the figures of the accompanying drawings, in which.

DETAILED DESCRIPTION OF THE DRAWINGS

Figure 1:
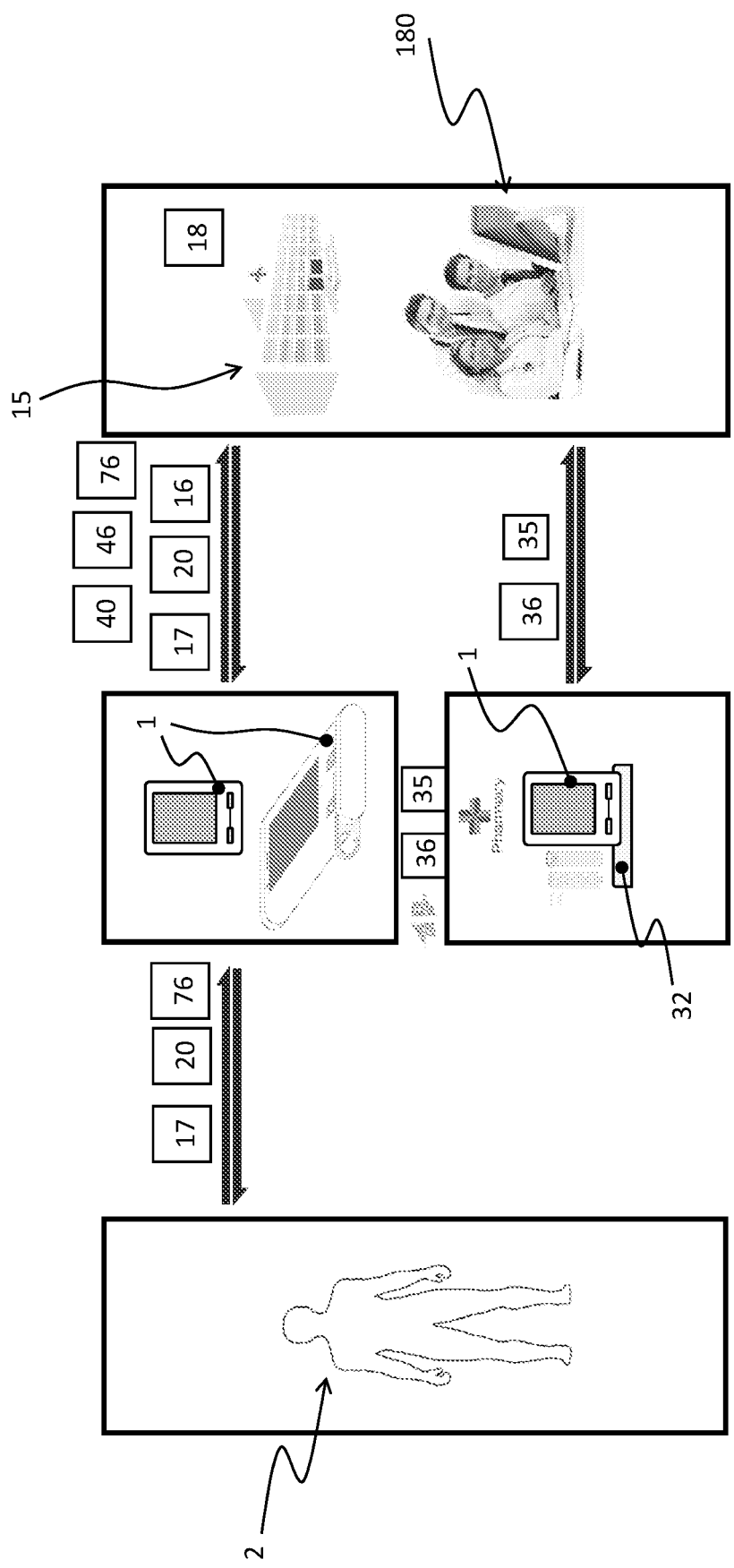
FIGS. 1 and 2 represents a general scheme of all aspects of exemplary embodiments of the present invention and their mutual correlation.

Making reference to FIG. 1, it is schematically and synthetically depicted the present invention according to exemplary embodiments.

In particular, it is illustrated an exemplary embodiment of a medicament dispenser, according to the present invention, denoted with numeral reference 1.

Medicament dispenser 1 enables real-time control and monitoring of medicine or drugs (in this document generally referred to as "medicament") for a user 2 in accordance to a medical prescription, per each single delivery and per dose. It may also apply to pharmaceutical products in general as detailed above.

As it will be described in details in the following, the medicament dispenser 1 comprises means for communicating data with a remote server 15.

The remote server 15 may be typically located in a hospital/clinic facility or in general at a location accessible to a doctor/medical staff 180, as administrators of the device, or by automatic programmed decision making based on predefined situations, such to enable monitoring and/or control of single, or set, of deliveries and enabling the doctor/medical staff to know when the patient effectively took the defined/prescribed medicament, as well as monitoring the effects of such intake in patient's body.

The medicament dispenser according to the invention additionally enables the remote control and monitoring of exceptional deliveries of doses out of standard dose, as well as out of prescribed scheduled timing.

User 2 authenticates him/herself by inputting in the medicament dispenser 1 user authentication data 76.

User 2 is associated to a dispensing protocol, generally indicated with numeral reference 18. Dispensing protocol 18 includes a set of pre-determined rules tailored on the user's medical needs, such as type and quantity of medicament to be taken at a fixed time schedule. Dispensing protocol 18 is generally defined by the doctor based on user's medical conditions. In some embodiments, medicament dispenser 1 enables the dispensing protocol 18 to be remotely varied by the doctor/medical staff 180 based on the real-time remote monitoring of user's medicament intake. Based on the dispensing protocol 18, a delivery control data 16 is elaborated and exchanged, along with user authentication data 76, between the medicament dispenser 1 and the remote server 15. Delivery control data 16 may generally be identified as a signal corresponding to medicament delivery instructions as well as stored information in the medicament dispenser 1 related to the occurred medicament delivery based on such instructions. Such data is sent/received from the medicament dispenser 1 to/from the remote server 15 to enable a real-time monitoring of the user's status.

Based on this monitoring activity, dispensing protocol 18 may be varied, and this may be reflected in the delivery control data 16.

In some embodiments, user 2 may also communicate to the medicament dispenser 1 health data 17 relative to his current physical state. As it will be described in the following, such health data 17 may be collected through an auxiliary device or via the medicament dispenser 1 itself, collecting for example user's visual data 20, for example by means of a camera as it will be described in the following. Health data 17, along with user's visual data 20 may also be exchanged between medicament dispenser 1 and remote server 15 for remotely monitoring user's physical conditions related to medicament intake based on the current dispensing protocol 18. Moreover, patient's conditions before and after medicament intake may be also monitored by pupilometry still by means of a camera.

In some embodiments, remote server 15 may establish to remotely terminate the delivery service via sending a signal corresponding to a service termination order 40 to the medicament dispenser 1, which disables the delivery of the medicaments. Service termination order 40 may be triggered in case, for example, of recorded abnormal usage of the medical dispenser 1 or in case of detected worsening of user's physical conditions.

In some embodiments, additionally or alternatively, remote server 15 may also send a signal corresponding to a destruction service order 46, which operates the internal physical destruction of the medicaments contained in the medicament dispenser 1.

Hence, medicament dispenser 1 according to the invention assures that the deliveries of medicines, namely strong medicines such as opioids pharma products, or other similar pharma products used for similar purposes, only occur according to its specific medical prescription, in terms of dose per delivery, and its frequency, to the specific user as the known patient, recognized as so by the doctor/medical staff through the remote server 15, as well as it enables to monitor and control such deliveries by one, or more, administrative authorized personnel that may also control the dose, and change it if necessary upon extraordinary situations which can be identified in real time, and assessed remotely while remotely accessing to health data of the user as patient. These core features enable that a third party such as a medical professional individual, or equivalent professional working in a clinic/hospital, may access critical health data of the patient and take the most adequate medical decisions towards his/her health and wellbeing in the specific situation, in a safe way, also enabling monitoring of the results of such decisions, and act accordingly in case of any exceptional abnormal situation.

Still with reference to FIG. 1, in accordance to a further aspect of the present invention, it is illustrated a medicament re-filling apparatus 32 for use with the medicament dispenser 1. Medicament re-filling apparatus 32 is configured to operate a re-fill of medicaments into the medicament dispenser 1 and it is typically located at authorized sites such as pharmacies or the like. To this aim, medical dispenser according to the invention is advantageously provided in the form of a portable device, which allows the use to conveniently carry it to the authorized site for re-filling operations.

More in particular, re-filling apparatus 32 is configured to exchange validation data 35 between the medicament dispenser 1 and/or the remote server 15 for running the necessary check for recognition of the medicament dispenser 1, the user 2 and the pre-defined dispensing protocol 18. If all the checks are successful, then re-filling apparatus 32 may send an authorization signal 36 to unlock the medicament dispenser 1 in order to allow the medicament re-filling operations.

Figure 2:
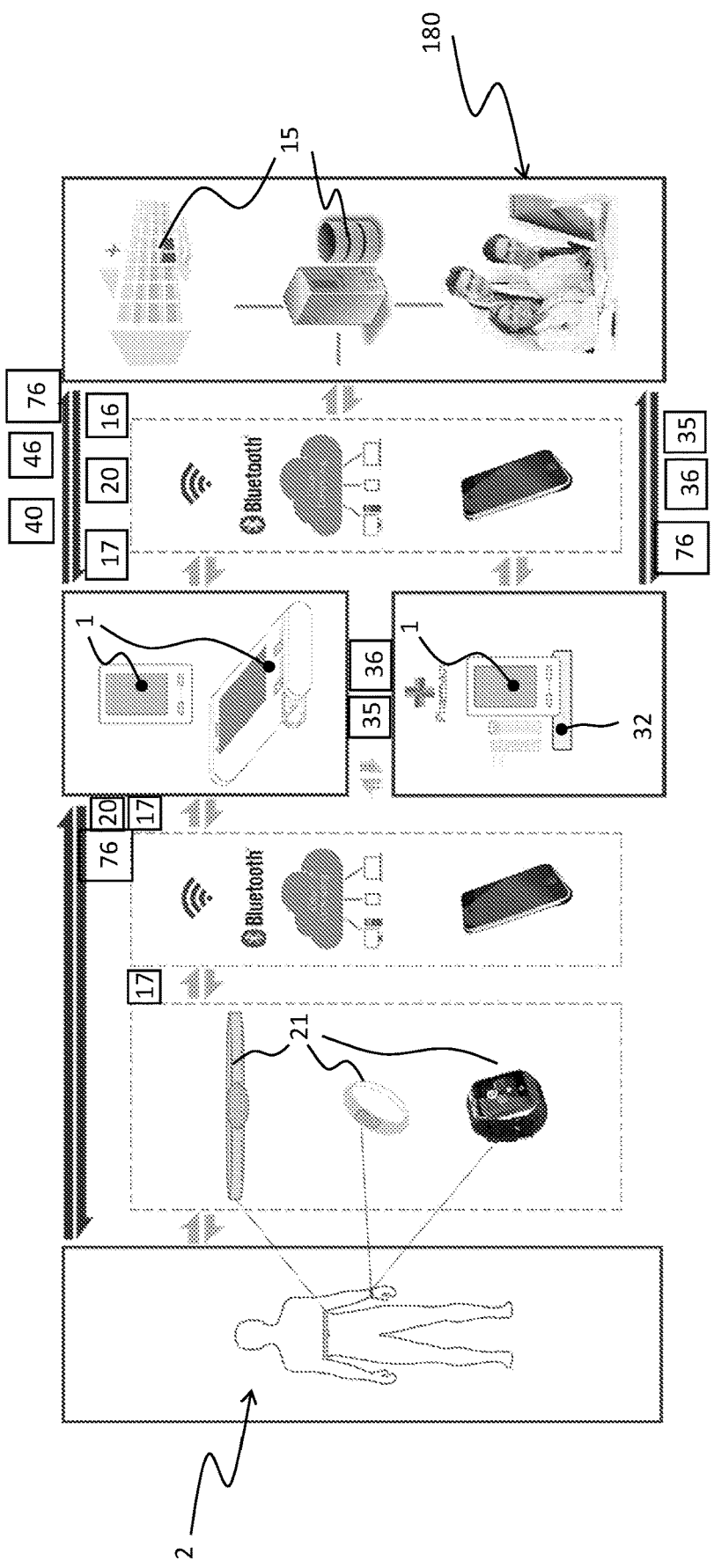

With now reference to FIG. 2, it is illustrated in more details the scheme of FIG. 1.

In some embodiments, medicament dispenser 1 may be configured to exchange data, such data comprising (but not limited to) control delivery data 16, health data 17, user's visual data 20, service termination order 40, destruction service order 46, through wireless means. More in particular, known communication media may be used for the purpose, such as a Bluetooth and/or a Wi-Fi type of connections, an accessible Cloud storage on the internet or through smart devices connection, enabling communication between medicament dispenser 1 and remote server 15. Similar types of communication interfaces may be used for authenticating the medicament dispenser 1 for re-filling operations: medicament re-filling apparatus 32 may exchange data with the medicament dispenser 1 and/or the remote server 15 through above-mentioned known communication interfaces.

It will be appreciated that those who are skilled in the art have the sufficient knowledge to implement such technologies into the present invention to enable data communication between, for example, the medicament dispenser 1, the remote server 15 and the medicament re-filling apparatus 32.

In some embodiments, user 2 may also be equipped with auxiliary devices, generally denoted with numeral reference 21, configured to collect vital health data 17 from the user 2. Auxiliary devices 21 may include a wearable device 21, configured for such purpose. Advantageously, medicament dispenser 1 may also be provided together with an auxiliary device 21 in combination, in order to provide user 2 with a complete medical system.

It will be appreciated that such technology, namely wearable devices capable of monitoring the physical being of a user 2 by collecting characteristics such as the heartbeat, are known to those who are skilled in the art and a detailed description thereof will be omitted in the present document.

In some embodiments, auxiliary device 21 may exchange health data 17 with (but not limited to) the medicament dispenser 1, the medicament re-filling apparatus 32 and the remote server 15 through wireless means, as detailed above.

Figure 3:
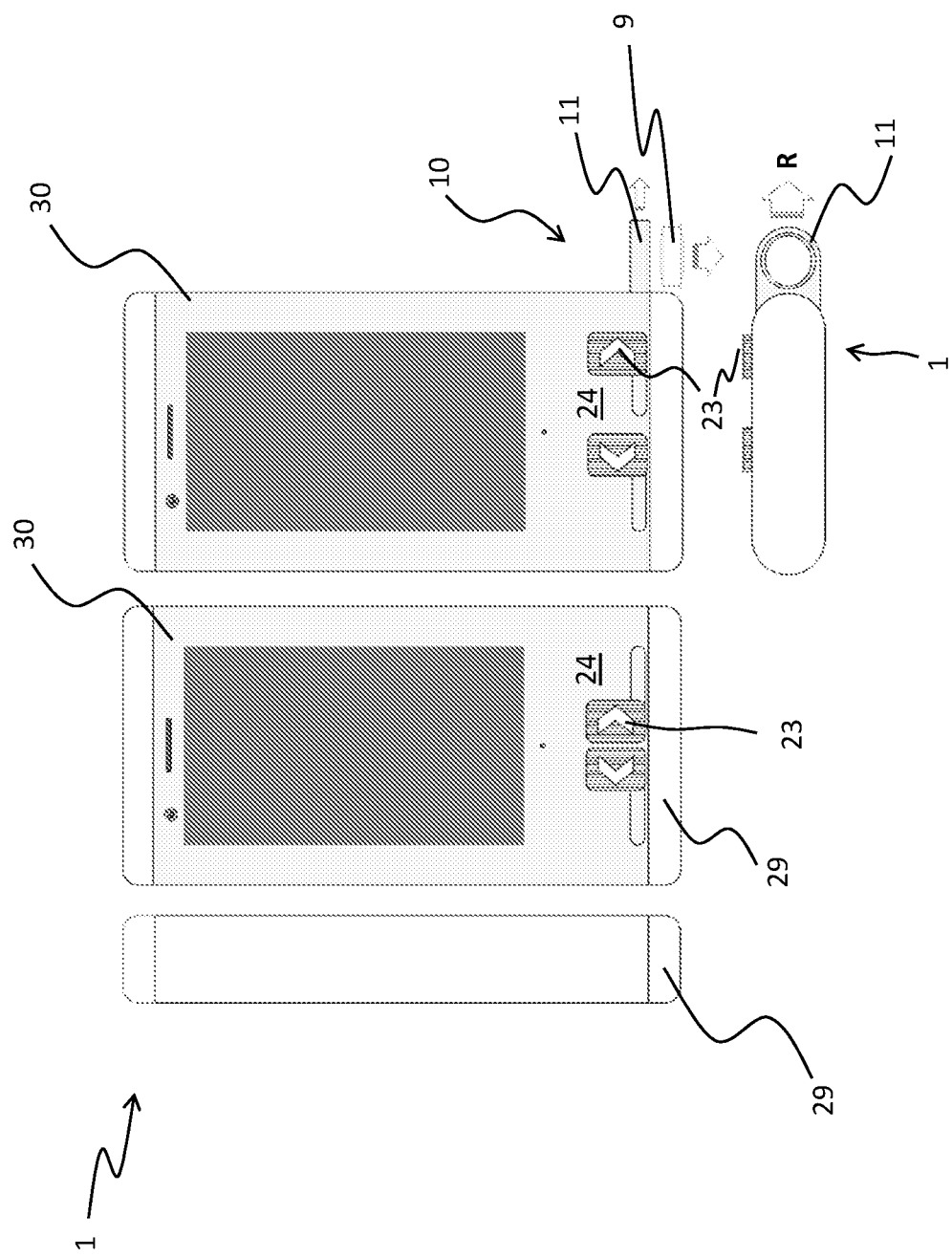
FIGS. 3-4 and 18, 20 show front views of the medicament dispenser according to exemplary embodiments.

With reference to FIG. 3, it is shown a medical dispenser 1 in a lateral, front and top view according to an exemplary embodiment.

Generally, medicament dispenser 1 comprises a main body 30 and a removable cover 29. In this exemplary embodiment, main body 30 internally includes a storage for storing medicaments.

Removable cover 29 is adapted to be removed only under pre-defined conditions, which will be better detailed in the following, to enable access to the internal storage of the medicament dispenser 1 and operate re-filling of medicaments.

In the embodiment shown as a non-limiting example, medicament dispenser 1 is configured to accept medicaments in the form of a tablet 9.

However, still remaining within the inventive concept underlying the present invention, medicaments may have different forms other than tablets.

As a non-limiting example, medicament dispenser 1 may deliver medicament containing one or more active agents in the following forms:
Solids: tablets and pills, compressed in any type of geometric shapes and sizes, including:
coated tablets;
multilayer tablets with combination of different active agents;
chip tablets, smart tablets of any form, including IEM (Ingestible Event Markers);
enteric coated tablets, including MUPS (Multiple Unit Pellet Systems);
Powders: including as salts, in micro and/or nano particles sizes, including:
inside capsules;
encapsulated in micro-capsules in capsules;
granulated as granules in capsules; and
as free powder in canisters or cartridges, including with compressed air or gases.
Liquids: in several viscosity and fluidity forms, including:
in containers, including in blistered containers, canisters, and cartridges; and
in capsules.

Liquid forms may be used for intravenous injection, or for inhaled aerosol route via the mouth, or mouth and nose.

Medicine in aerosol forms, namely produced by thermal aerosolization based on electrical resistive heat or induction heating systems, or nozzles dispersing liquids from pressurized containers, pumps or micro-pumps, as well as aerosols produced using ultrasound systems, may be used in case of patients requiring opioids for:
the relief of dyspnea due to chronic pulmonary or cardiac disease;
the relief of dyspnea due to primary or metastatic pulmonary neoplastic disease;
the prevention or relief of pain due to neoplastic disease.

Concerning medication in tablet forms, depending of the targeted organ, or organs, where the active agent, or agents, are supposed to be delivered, absorbed and/or adsorbed, active agents in tables may be intended for standard use as tablets, including as dispersible tablets, as well as for sublingual intake.

Broadly speaking, medicament dispenser according to the present invention may use several types of medicaments, as consumables, including:
One, or more, types of consumables with one, or more, type of active agent(s).
Example 1: a pain medicine, such as an opioid, as consumable "A" in a form of tablet, and a medicine to help pain medicine performance, as consumable "B", such as a bisphosphonate (e.g. dexamethasone), in a form of tablet.
Example 2: a pain medicine, such as an opioid, as consumable "A" in a form of Film, dermatologic patch, and a medicine to help pain medicine performance, such as a bisphosphonate (e.g. dexamethasone), as consumable "B" also in a form of tablet.
Example 3: a pain medicine, such as an opioid, as consumable "A" in a form of tablet, in a dose of 10 mg, and the same or similar type of medicine in a form of tablet but with a stronger dose of 20 mg, as consumable "B". Alternatively, such extraordinary dose may be of a lighter dosage of the same medicament, or a defined dose of a different medicament, as a complementary medicament, such as an analgesic, etc.

Still with reference to FIG. 3, medicament dispenser 1 comprises a dispensing unit 10. Dispensing unit 10 is configured to access the internal storage of the medicament dispenser 1 (not visible in the figure) and dispense the medicament 9. In this exemplary embodiment, dispensing unit 10 comprises an ejector 11 which is connected to a slidable button 23, manually operable by the user, to extract medicament 9. As shown, slidable button 23 is located on an external wall 24 of the medicament dispenser 23.

Figure 4:
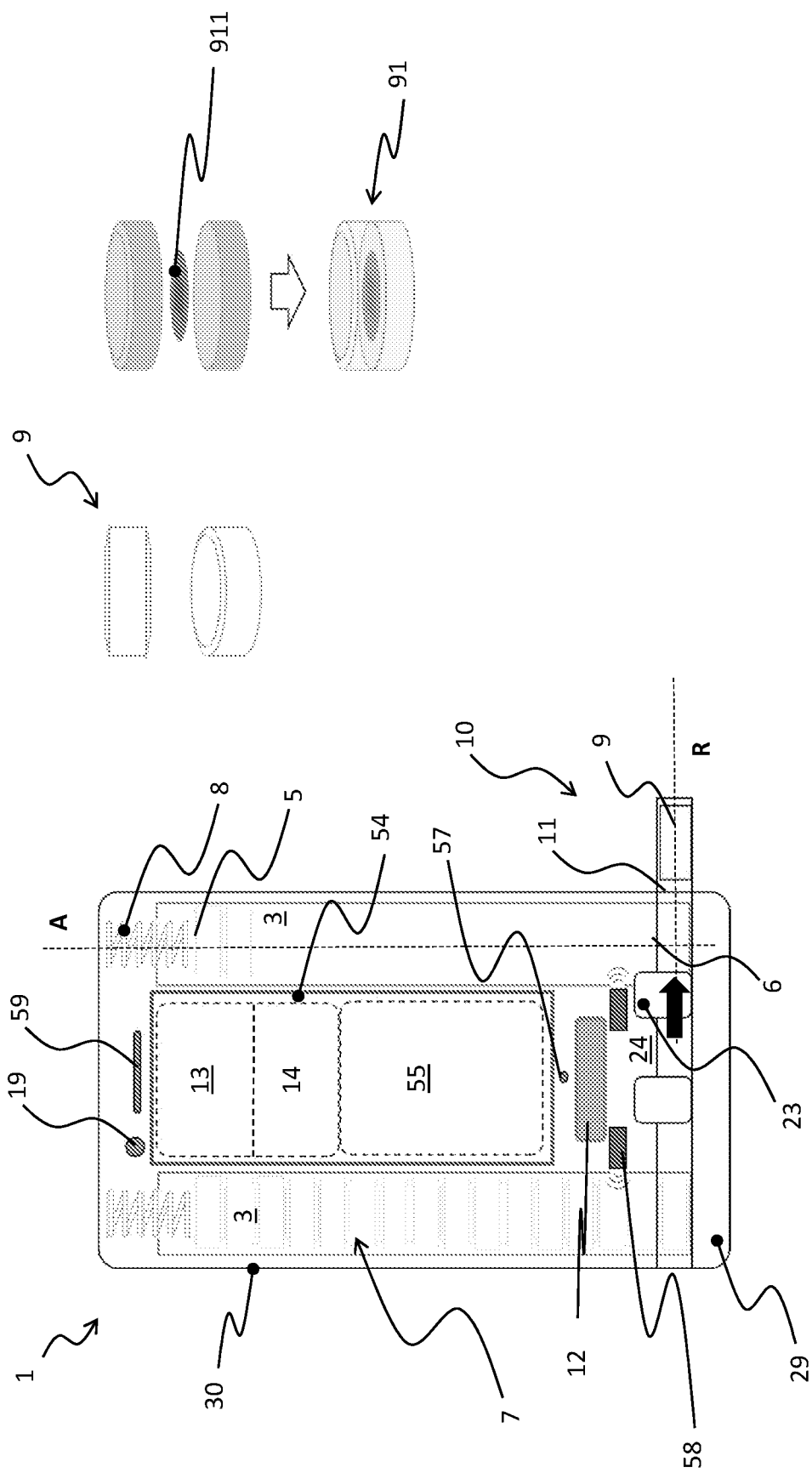

Making now reference to following FIG. 4, which shows a front view of the medical dispenser 1, also revealing its internal parts.

More in particular, main body 30 of medicament dispenser 1 includes an internal storage, now visible and depicted with numeral reference 3, for storing one or more medicaments 9. In the exemplary embodiment shown, medicament dispenser 1 comprises two internal storages 3, however it will be appreciated that the medicament dispenser 1 according to the present invention may comprise any number of internal storages. Description will follow relative to one storage, because the same description shall apply to any storage shall the dispenser 1 include more than one.

In this exemplary embodiment, internal storage 3 is in the form of an elongated compartment, having a top end 5 and a bottom end 6. The compartment 3 is adapted to accommodate a plurality of tablets 9 in the form of a pile 7.

Ejector 11 of dispensing unit 10 is configured to slide in a reciprocating fashion along a direction R, which is transversal to an axis A of the elongated compartment 3. In the specific, ejector 11 is slidable from an inner position inside the main body 30 where it collects the medicament 9 located at the bottom end 6, to an outer position where the ejector 11 protrudes out of the dispenser 1 to deliver the tablet 9 for user intake.

Advantageously, compartment 3 further includes a resilient means 8 located at the top end 5 such to exert a pressure on the tablet pile 7 and to ensure that the tablet 9 located at the bottom end 6 of the compartment 3 is intercepted by the ejector 11 when in the inner position for medicament delivery. Ejector 11 is operable by the user by a slidable button 23 located on the external wall 24 of the main body 30. With reference to the figure, the slide of button 23 in the direction of the arrow causes delivery of a tablet, whilst a slide in the opposite direction is needed for loading the ejector of a tablet still within the pile 7 for a next delivery.

In the figure, it is depicted by way of example a normal tablet 9 and chip tablet 91, including an ingestible event marker 911.

In some preferred embodiments, medicament dispenser 1 may also comprise a sensor 58 adapted to detect presence of medicaments in the bottom position just before delivery for consumption. In case of usage of chip tablets 91, sensors may also recognize those tablets 91 by chip reading/connectivity.

In some preferred embodiments, medicament dispenser 1 may comprise a microphone 57 for audio signal input, a loudspeaker 59 for audio output and a display 54 for enhancing/optimizing the user interface with the dispenser 1.

Medicament dispenser 1 comprises a control unit 13, powered by a power supply, such as a battery, 55.

Control unit 13 includes a user recognition unit, generally indicated with numeral reference 12, for collecting user authentication data. User recognition unit 12 may use different types of existing technologies for this purpose. In this exemplary embodiment, user recognition unit 12 includes a fingerprint reader for bio-metric authentication. Alternatively or additionally, user recognition unit 12 may include the display 54, which may be equipped with touch-screen capabilities, for enabling the user to input a password and thus being recognized.

Control unit 13 further includes a communication module 14 configured to send/receive user authentication data and delivery control data associated to the predefined dispensing protocol to/from the remote server.

Control unit 13 is a processor which is adapted to receive/elaborate user's authentication data gathered from the fingerprint reader 12 and to drive the communication module 14 for sending/receiving delivery control data and user authentication data associated the predefined dispensing protocol to/from the remote server.

In this exemplary embodiment, communication module 14 is configured to send/receive delivery control data and user authentication data to/from the remote server through wireless means, as above explained. Control unit 13 further comprises a storage unit for storing historical data about medicaments delivery and consumption. Advantageously, historical data is also exchanged with the remote server 15, in order to enable doctor/medical stuff to monitor the user's intake throughout his/her medical treatment.

In some preferred embodiments, medicament dispenser 1 may also comprise a camera 19 for detecting user's visual data which is associated to user's physical characteristics. In such embodiments, advantageously, control unit 13 may also be configured to process visual data in order to obtain health data of the user. For example, the degree of dilatation of the pupil, which may be controlled by camera 19, may be an indication of the state of being of the user. Control unit 13 is adapted to enable/disable the dispensing unit 10 based on user authentication data and delivery control data exchanged with the remote server. Said differently, if user's recognition is not successful, and/or the dispensing protocol for the particular user does not include delivery instructions, then dispensing unit 10 is not be enabled for medicament delivery.

To this aim, with reference to this exemplary embodiment, medicament dispenser 1 comprises a blocking device associated to the ejector 11 of dispensing unit 10, which is adapted to prevent/allow movement of the ejector 11 when activated/de-activated by the control unit 13.

Figure 5:
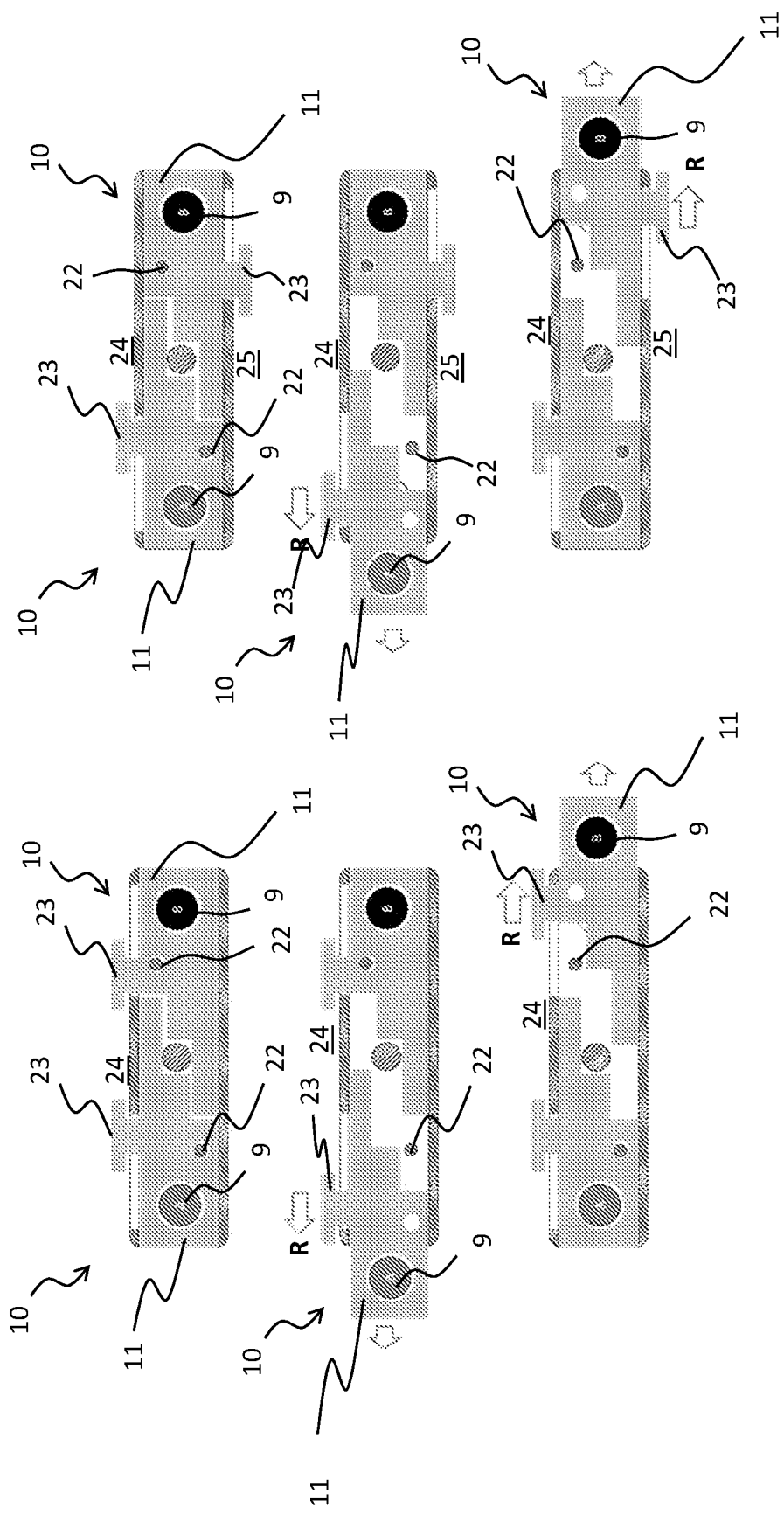
FIG. 5 shows a top view of a blocking system, as cross section showing the related main parts and components, of the medicament dispenser according to an exemplary embodiment.

Next FIG. 5 shows an exemplary embodiment of a blocking device associated to the dispensing unit 10. FIG. 5 shows a top-view section of medicament dispenser 1. Particularly, two different exemplary embodiments are shown: on the left a medicament dispenser having two compartments where ejectors 11 are operable by slidable buttons 23 located on the same external wall 24 of the dispenser, and on the right a medicament dispenser having two compartments where ejectors are operable by slidable buttons 23 located on opposite walls of the dispenser, that is walls 24 and 25. Description of blocking device will be directed to a single ejector 11, and the same applies to all the ejectors 11 in any configuration.

Blocking device comprises a blocking pin 22 which is receivable into a correspondent hole positioned in the ejector 11. Blocking pin 22 is movable between a delivery position, where it is released from the ejector 11 and allows its movement (driven by the user through slidable button 23) to eject a tablet 9 (by movement in the direction indicated by arrow R), and a blocking position where it is inserted into the ejector hole, thus preventing its movement. Position of blocking pin is driven by the control unit, based on data collected by the user and exchanged with the remote server associated to dispensing protocol.

Alternatively, button 23 may be in the form of a rotatable knob. More specifically, its rotation may drive the slide of the associated ejector 11 to dispense tablet 9 as above detailed.

Figure 6:
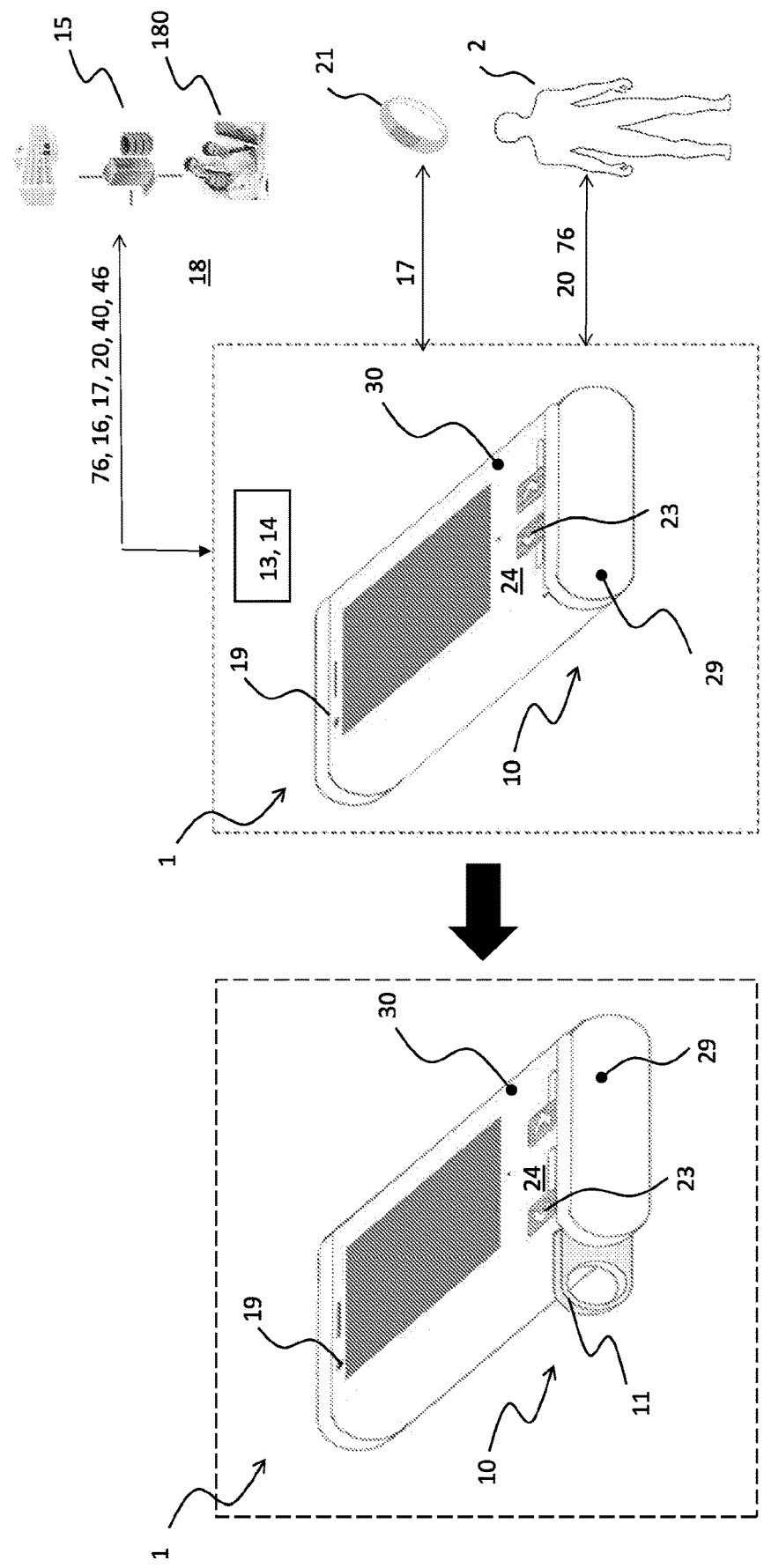
FIGS. 6, 19 and 21 show perspective views of a medicament dispenser according to exemplary embodiments of the present invention and it schematically illustrates a usage thereof.

With now reference to FIG. 6, it is illustrated the medicament dispenser 1 and schematically illustrated an exemplary usage thereof.

User 2 accesses the medicament dispenser 1 and authenticates his identity by input of his/her user authentication data 76. In some embodiments, health data 17 collected by the wearable device 21 may also be input into the medicament dispenser. In some embodiments, medicament dispenser 1 may also be provided with a camera 19 for detecting user's visual data 20. Control unit 13 collects user authentication data 76 and user health data 17 and exchange such piece of information through communication module 14 with the remote server 15. Remote server 15 elaborates the information and, based on the dispensing protocol established with the user 2, inputs control delivery data 16. It will be appreciated that, based on current user's health data 17, dispensing protocol 18 may be varied, thus affecting the delivery control data 16. As an example, if health data 17 is considered abnormal, medicament delivery may be interrupted.

If all conditions are met and control delivery data 16 contains instructions for a medicament delivery, then control unit 13 de-activates blocking device of the ejector 11. User 2 may act on slidable button 24 to guide extractor 11 out of the dispenser 1 and collect the medicament.

In some preferred embodiments, communication module 14 may further comprise a sub-unit configured to enable voice communication and/or text communication and/or video communication between the user 2 and the medical staff 180, namely the doctor who is remotely monitoring the dispensing protocol 18 of the user 2.

For example, sub-unit of communication module 14 may include a cellular module configured to enable a voice call and/or text messages and/or a video call over a cellular network between user 2 and the doctor 180. Alternately or additionally, sub-unit may be further configured to enable communication over an internet connection, for example through a Wi-Fi type of connection.

Advantageously, the monitoring of the effective intake of the medicine, as well as the general medical conditions of the authenticated user 2, may be possible by assessing the health data 17 acquired by the auxiliary external devices 21 interfacing with the medicament dispenser 1.

Additionally or alternatively, the monitoring of the effective intake may also be assessed by a direct voice and/or visual remote interaction between the user 2 and the administrator 180. Specifically, this is made possible by the sub-unit of communication module 14 enabling such type of remote communication.

Said differently, sub-unit of communication module 14 adds to the medicament dispenser 1 functionalities currently existing in known mobile phones.

This further technical feature is particularly advantageous in the following exemplary scenario.

User 2 may be in the strong need of an additional medicament intake, which may not be included in the current dispensing protocol 18. He/she may have the option of directly contacting medical staff 180 by means of a voice or a video call, using the portable medicament dispenser 1 according to the present invention which is equipped with sub-unit of communication module 14 enabling a voice call. To this aim, the above-underlined portability of the medicament dispenser according to the invention is particularly useful because it enables the user to utilize the dispenser 1 as a normal mobile phone. In this way, user 2 may directly inform the medical staff 180 about the urge, and a decision may remotely be taken in a timely fashion. To this purpose, user 2 may be required to collect current health data 17 and send such data to the remote server 15 so that his/her physical state may be promptly evaluated by medical staff 180. This may be achieved by collecting user's pupil characteristics via the camera 19 of the medicament dispenser 1, as above detailed.

After health data 17 has been provided, a decision concerning an extra dose may be taken.

If a further intake is allowed, then it may be advantageous to require the user to collect health data 17 immediately after the intake of the extra dose and to send the latter to the remote server 15.

The entire procedure may advantageously occur with the help of a voice communication between the user 2 and the medical staff 180.

Furthermore, medicament dispenser 1 may advantageously also include a geo-localization system. Hence, location of the user 2 may easily be assessed by the medical staff 180 particularly in case of medical urgency, or in case of misuse of the dispenser.

Figure 7:
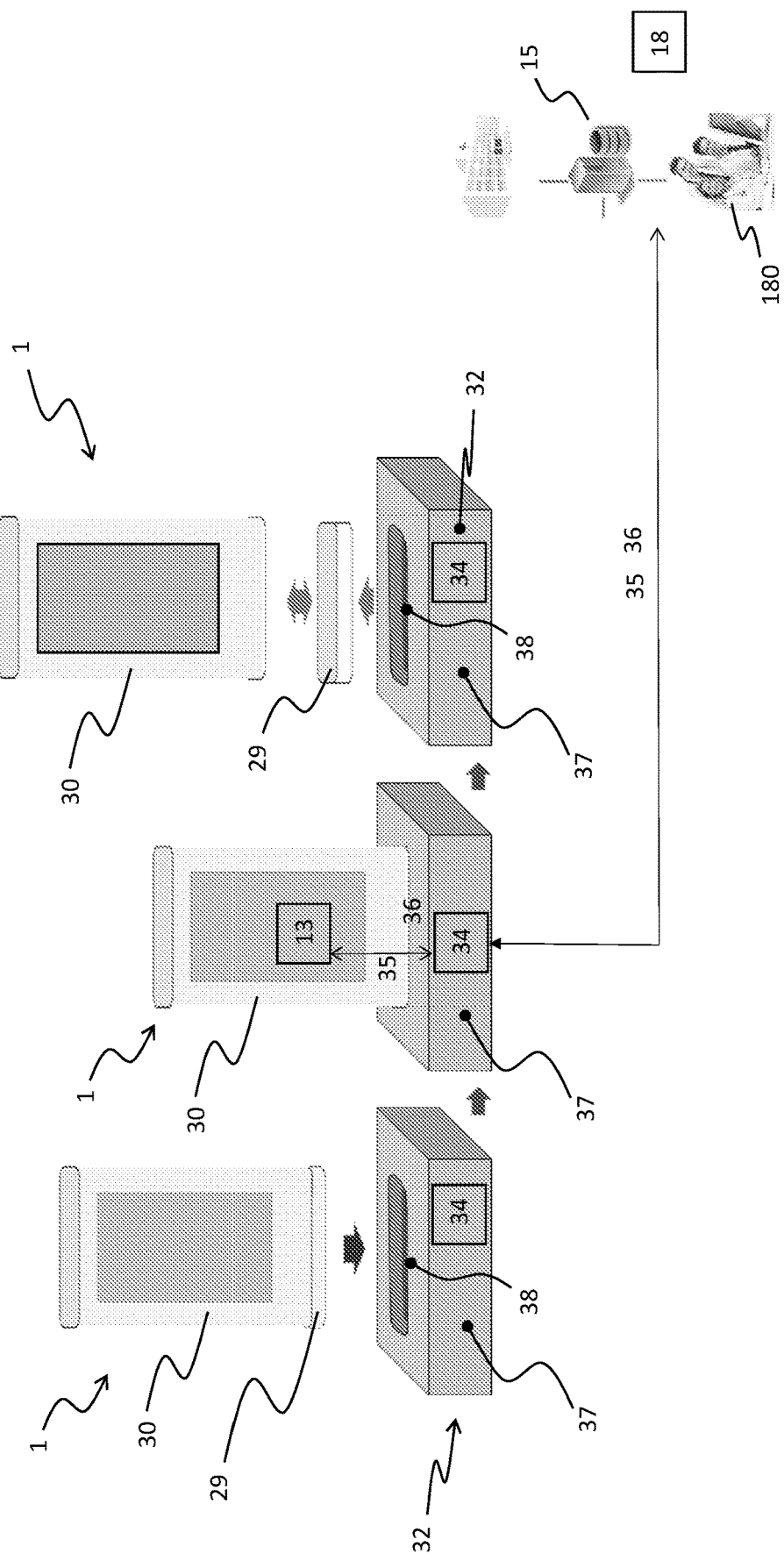
FIGS. 7, 8 and 12, 13 illustrate the medicament dispenser utilized with a re-filling apparatus according to an exemplary embodiment of the present invention.

With now reference to next FIG. 7, it is depicted the medicament dispenser 1 for a medicament re-filling operation. Medicament dispenser 1, as already mentioned, comprises a main body 30, including one or more storages for accommodating medicaments, and a removable cover 29 for accessing the storages. Removable cover 29 is connected to main body 30 by locking/unlocking means.

When cover 29 of the medicament dispenser 1 is removed, it enables the access to the compartment(s) that contain the medicaments, and therefore enabling to load the medicament dispenser with consumables for the first time as well as to reload/refill the dispenser with medicaments.

In some embodiments, locking/unlocking means associated to cover 29 may include RFID or AM/RFID, fitted with an ultra-high frequency (UHF) RFID antenna for use in AM EAS and AM RFID, used in common magnetic or electro-magnetic systems for unlock and detach secured locking devices as well as in electronic tag surveillance. It will be appreciated that such locking/unlocking means is known to those who are skilled in the art, and in this document a detailed description thereof will be omitted.

Advantageously, locking/unlocking means is configured to cooperate, for connecting/removing the cover 29, with the external medicament re-filling apparatus 32, only when the latter is located in physical proximity with the medicament dispenser 1.

Medicament re-filling apparatus 32 comprises a detaching system (not shown) adapted to cooperate with the locking/unlocking means of the medical dispenser 1 to lock/unlock the cover 29, thus allowing access to the internal storages for re-filling operations.

Apparatus 32 comprises a communication system, schematically indicated with numeral reference 34, to exchange, preferably through wireless means, validation data 35 with the remote server 15 and/or the control unit of the medicament dispenser 1. Validation data 35 is needed to enable/disable the detaching system of the apparatus 32 and thus allowing removal of the cover 29.

In some embodiments, re-filling apparatus 32 comprises a base 37 and a receiving slot 38 for internally receiving a portion of the medicament dispenser 1. In this exemplary embodiment, detaching system is located within the receiving slot 38 which physically matches medicament dispenser 1. A portion of medicament dispenser 1 including the cover 29 is inserted therein.

After insertion, communication system 34 of the apparatus 32 exchanges validation data 35 between the control unit 13 of medicament dispenser 1 and the remote server 15, to authenticate the medicament dispenser 1 to be re-filled and to preferably also collect information about the associated dispensing protocol 18, needed by the authorized personnel for completing the re-filling operations.

Detaching system is enabled/disabled based on the validation data 35. More in the specific, if all checks are successful, detaching system is activated by an authorization signal 36 to unlock the cover 29.

Figure 8:
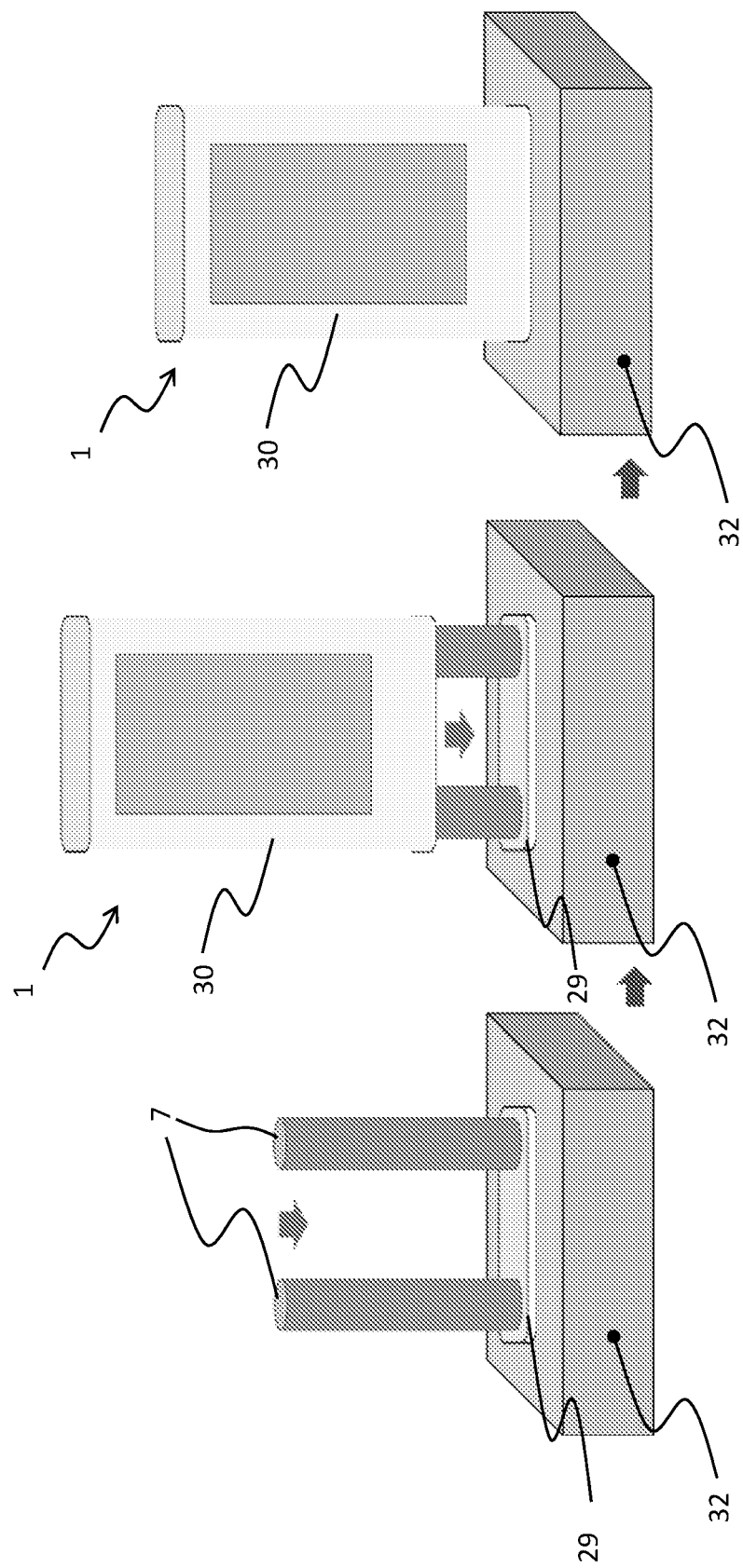

With reference to next FIG. 8, it is shown an example of re-filling operation. Two piles 7 of medicaments 9 are positioned on top of the cover 29. Next, medicament dispenser 1 is positioned back on the cover 29. Lastly, detaching system of apparatus 32 locks the cover 29 and the user may, at this point, leave the authorized site with the portable medicament dispenser 1 now re-filled with medicaments and ready to be used.

Figure 9:
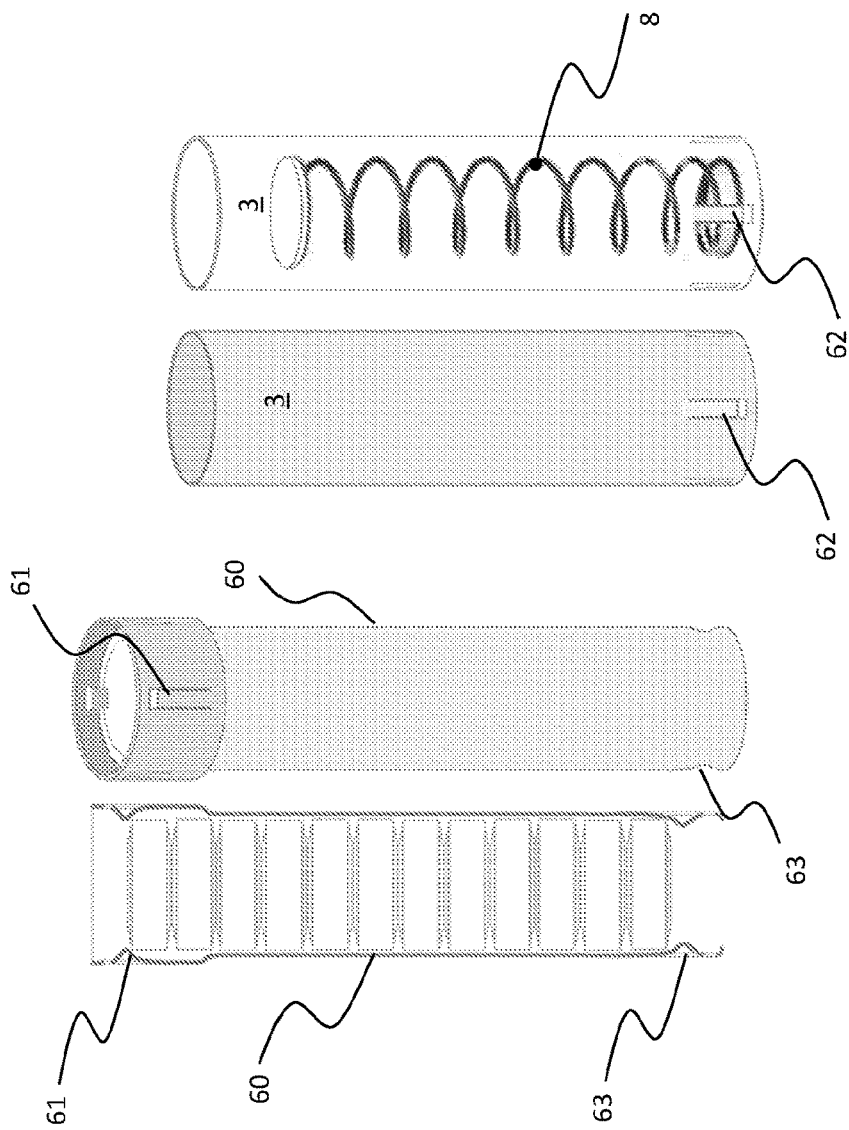
FIGS. 9, 10 and 11 show exemplary embodiments of medicaments for insertion into the medical dispenser.
Figure 9:
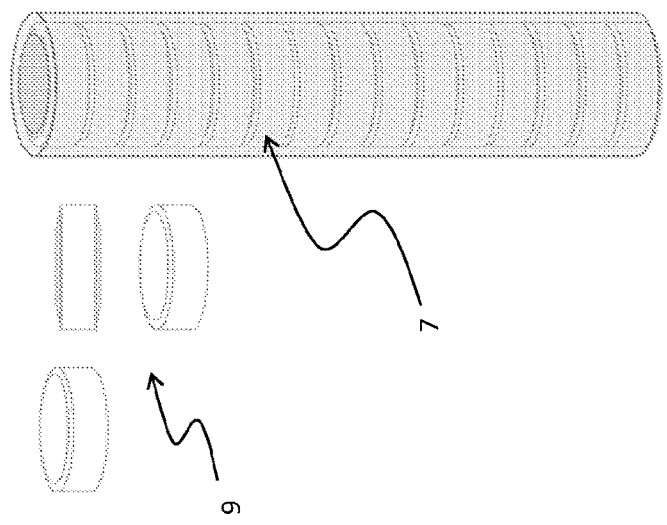

In some embodiments, making now reference to next FIG. 9, a pile 7 of medicaments 9 may be provided within a tubular cartridge 60, suitable for insertion within the elongated compartment 3, which may be manufactured, for example, in metallic or polymeric materials. Advantageously, pile 7 of medicaments 9 may be contained between a lower groove 61 and an upper groove 63. Correspondently, compartment 3 comprises an upper projection 62 which enters, during insertion of pile 7, into upper groove 63 such to stably hold the cartridge 60 therein.

Figure 10:
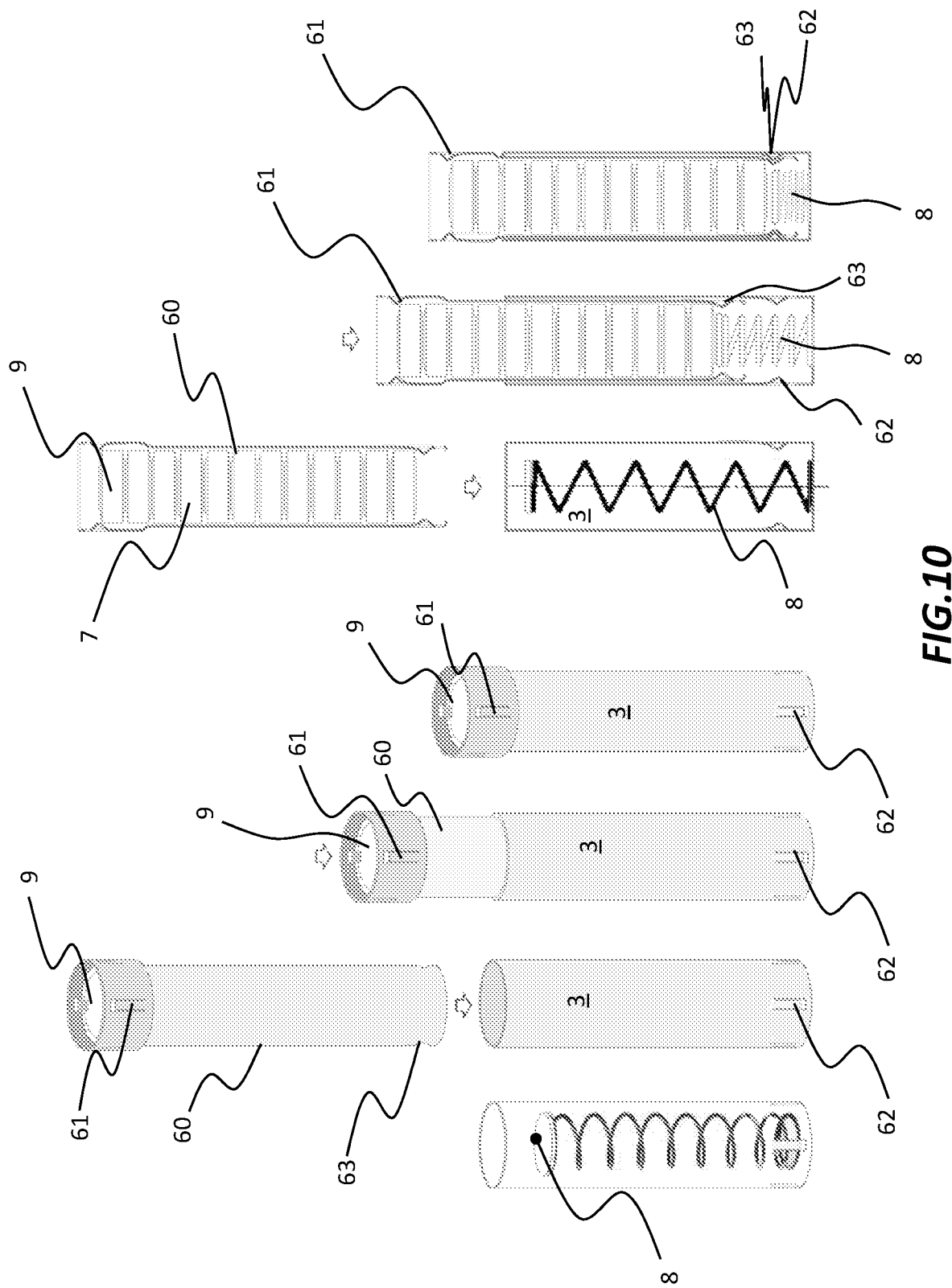

Insertion of cartridge 60 into compartment 3 is depicted in sequence with reference to next FIG. 10. In the figure, it is clearly shown that insertion of cartridge 60 compresses the resilient means 8 until upper projection 62 enters into upper groove 63. Insertion of projection 62 into groove 63 resembles a snap-fit type connection.

Figure 11:
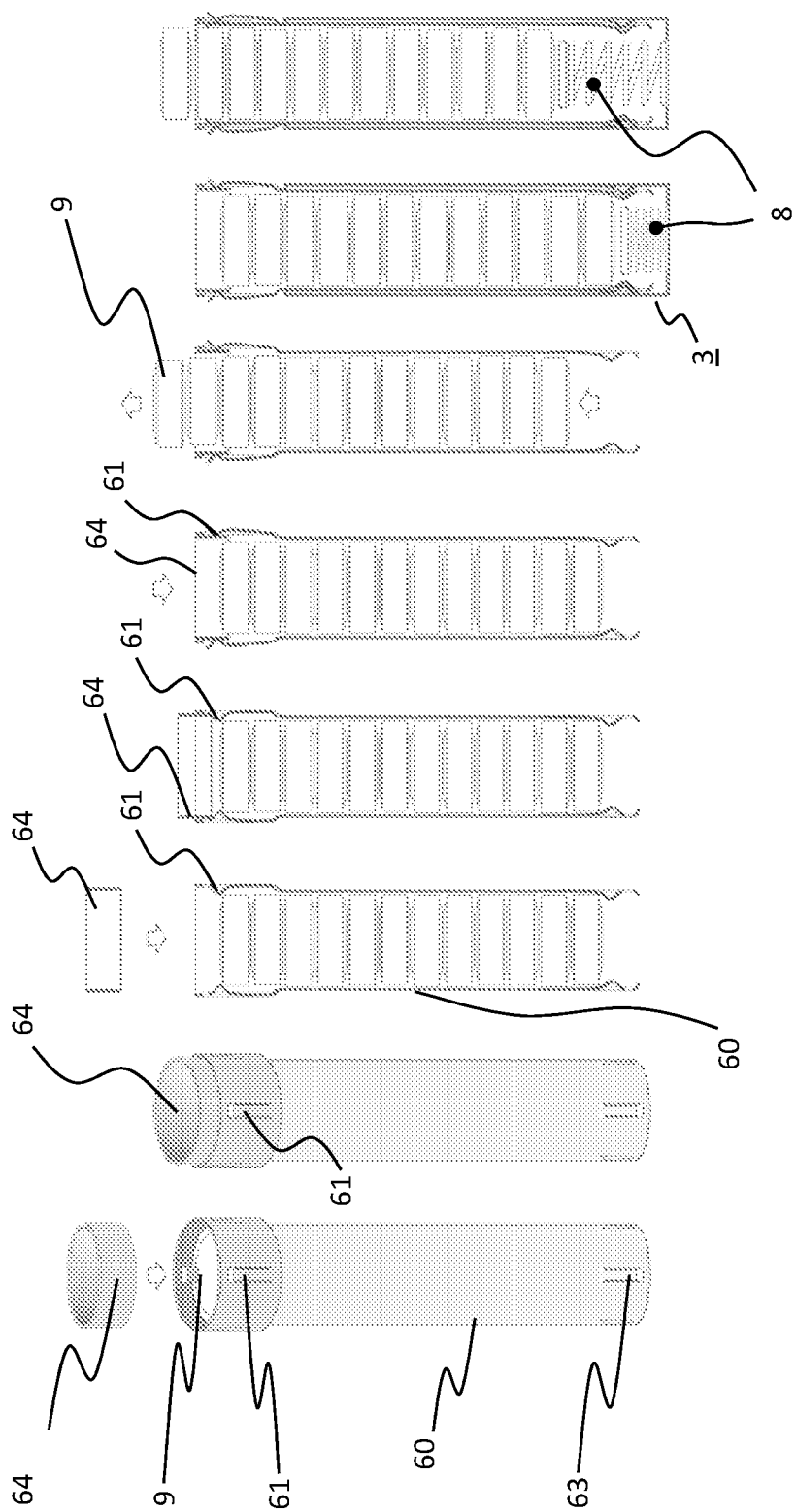

Making now reference to following FIG. 11, cartridge 60 is further equipped with a disarming ring 64. As it will be shown in the following, disarming ring 64 is forced within cartridge 60 such to disable lower groove 61 and enable delivery of tablets 9.

Figure 12:
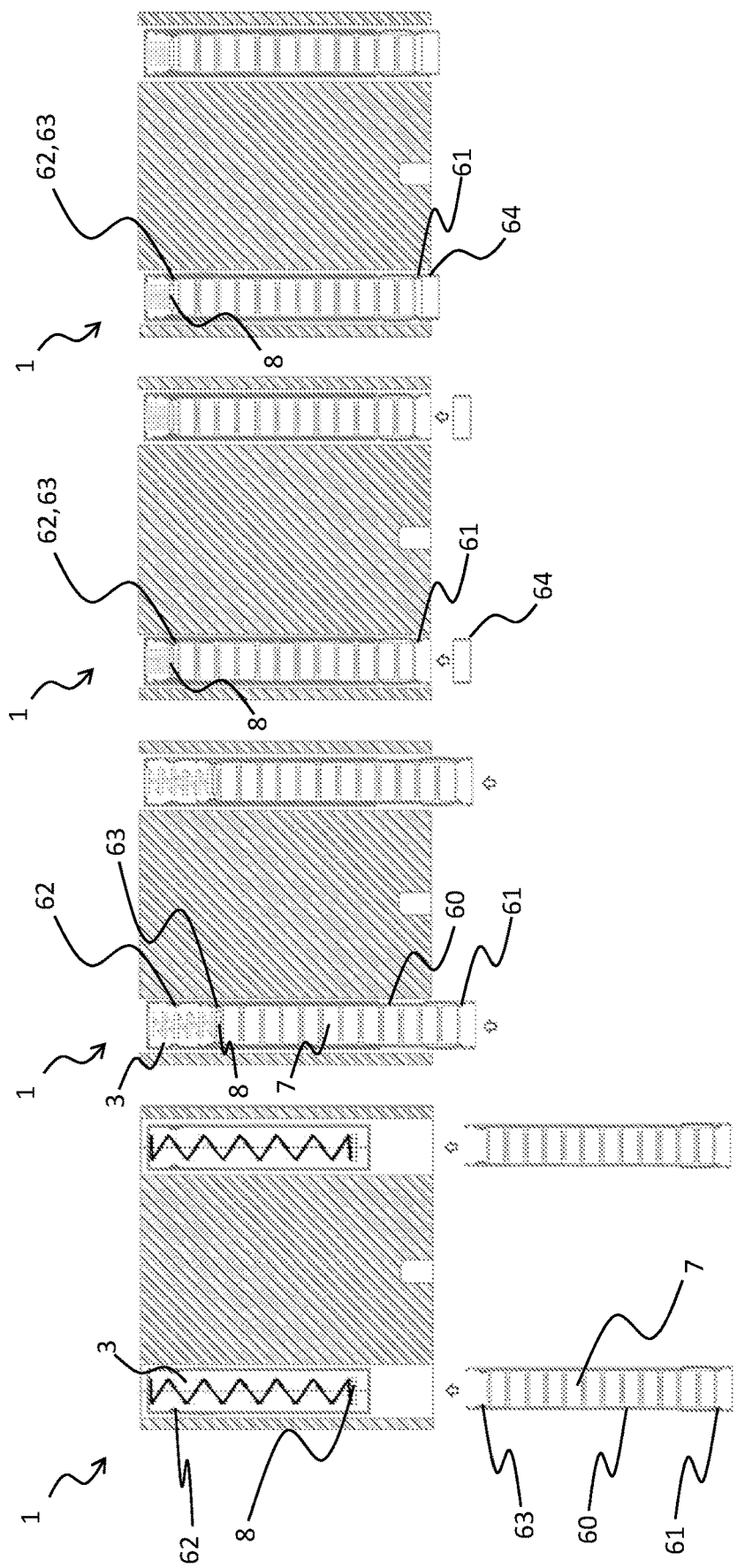

Next FIG. 12 shows insertion of cartridge 60 into compartment 3 of the medicament dispenser 1. Resilient means 8 is compressed until upper protrusion 62 of compartment 3 fits into upper groove 63 of cartridge 60. Subsequently, disarming ring 64 is put in portion in correspondence of lower groove 61. At this point, disarming ring 64 may be forced into the cartridge 60 manually by the user.

Figure 13:
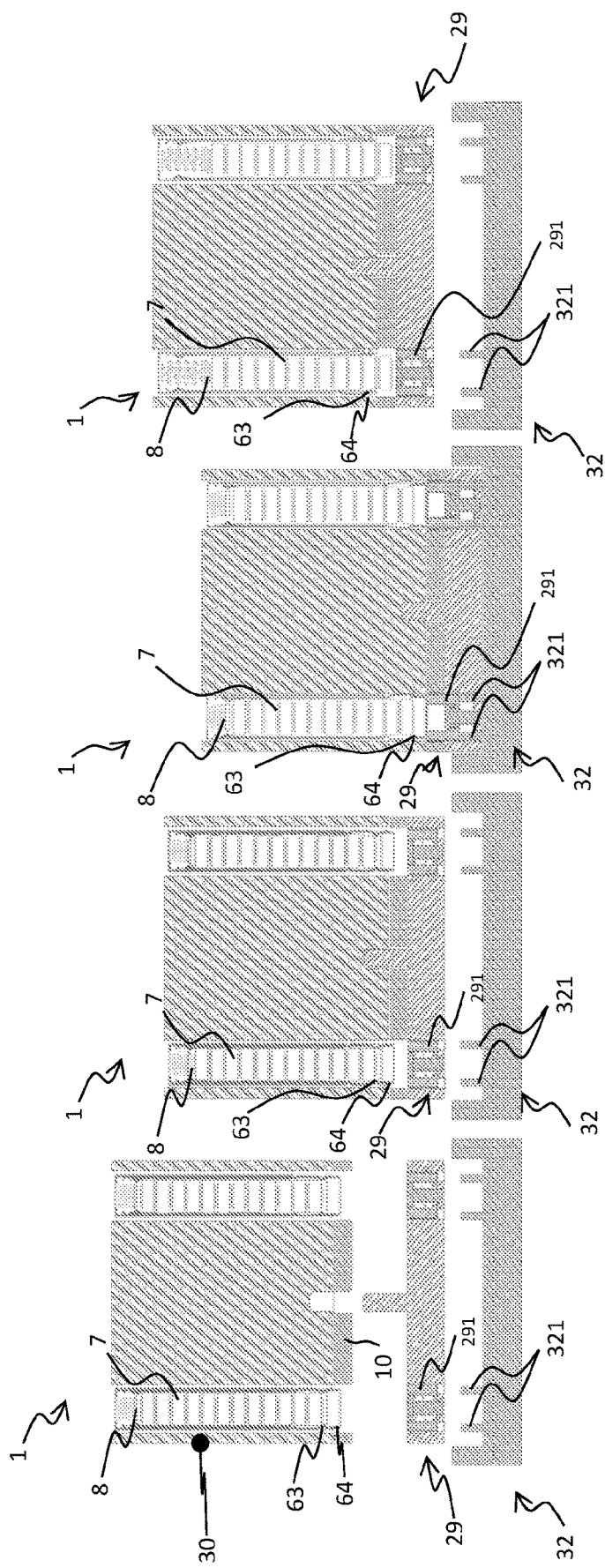

Alternatively, in some exemplary embodiments, as illustrated in next FIG. 13, forcing of disarming ring 64 into cartridge 60 may be operated automatically during connection of the main body 30 to the removable cover 29 operated by the re-filling apparatus 32, as detailed below. In the figure, which shows a front section of medicament dispenser 1, cover 29 and apparatus 32, the sequence of operation is shown from left to right.

Disarming rings 64 are firstly inserted in correspondence of lower groove 64 still without enlarging the cartridge 60 in a sufficient way such to allow delivery of the tablets. In this exemplary embodiment, cover 29 internally includes movable pins 291 which are free to project upward. Correspondently, re-filling apparatus includes within its receiving slot protrusions 321. Next, main body 30 is connected to cover 29. At this point, medicament dispenser is pushed inside the receiving slot of the re-filling apparatus 32 such to enable locking means for connecting the main body 30 to the cover 29. At the same time, protrusion 321 push upwards movable pins 291 which in turn act on disarming ring 64 and force the latter into the cartridge 60 such to disable lower groove 63. In this way, tablets may now be collected by dispensing unit 10, namely the ejector, for delivery.

Figure 14:
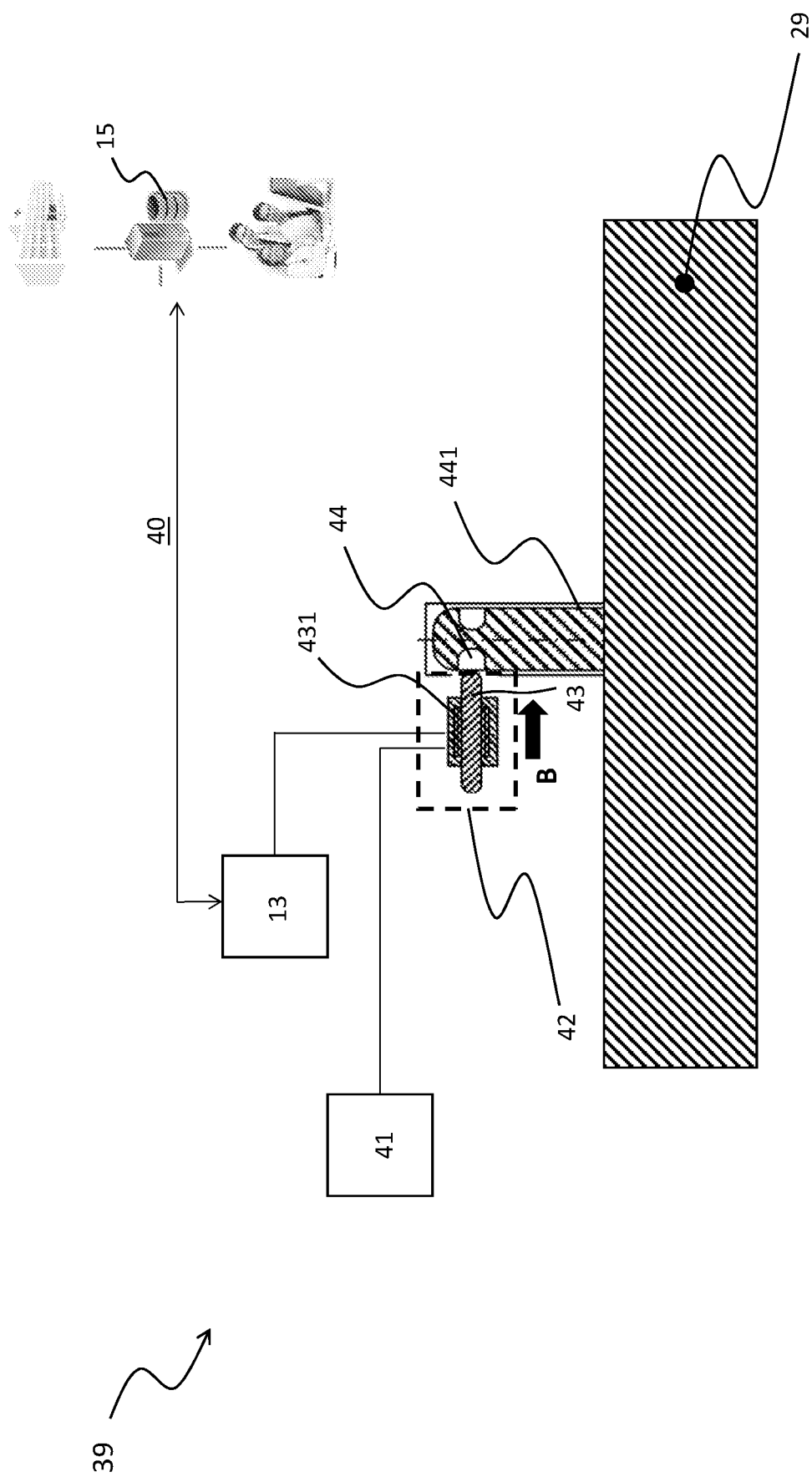
FIG. 14 schematically shows a safety clamping mechanism of the medicament dispenser according to an exemplary embodiment.

In some embodiments, with reference to following FIG. 14, medicament dispenser 1 may also comprise a safety clamping mechanism, generally denoted with numeral reference 39, which is configured to irreversibly prevent unlocking of the cover 29.

Safety clamping mechanism 39 may be activated by control unit 13 upon reception of the service termination order 40 sent by the remote server 15. Such service termination order 40 may be sent to the medical dispenser 1 in response, for example, to abnormal health data received from the user. In some scenarios, doctor/medical stuff may decide to immediately interrupt medicament delivery to assess user's physical conditions, without the risk of further medicaments intake.

In this exemplary embodiment, safety clamping mechanism 39 comprises an electro-mechanical switch 42, which includes a component 431 having a slidable pin 43. When the pin 43 is activated, it irreversibly slides along direction of arrow B into a groove 44 located on a portion 441 integral to the cover 29. The insertion of pin 43 into groove 44 prevents opening of the cover 29.

More in the specific, slidable pin 43 is constantly subject to a resilient force and it is maintained in the position depicted in the figure, namely out of the groove 44, by an electric circuit, schematically indicated with numeral 41, which produces a force opposed to the resilient one and keeps it in balance. Upon reception of service termination order 40, control unit 13 disables the electric circuit 41.

In this way, resilient force determines the irreversible slide of pin 43 within the groove 44 and thus the permanent unlocking of the cover 29.

In some embodiments, alternatively or additionally, the internal electric circuit 41, may advantageously be arranged in the medicament dispenser 1 such to detect a local attempt of hacking for removing the cover 29 and thus accessing the medicaments for unmonitored and uncontrolled intake. Safety mechanism 39 is activated is such attempt is detected. In fact, electric circuit 41 is advantageously located at an interface between main body and cover 29, and therefore an attempt of forcing the latter for its removal would cause breakage of circuit 41 and consequently the slide of the pin 43 within the groove 44.

Figure 15:
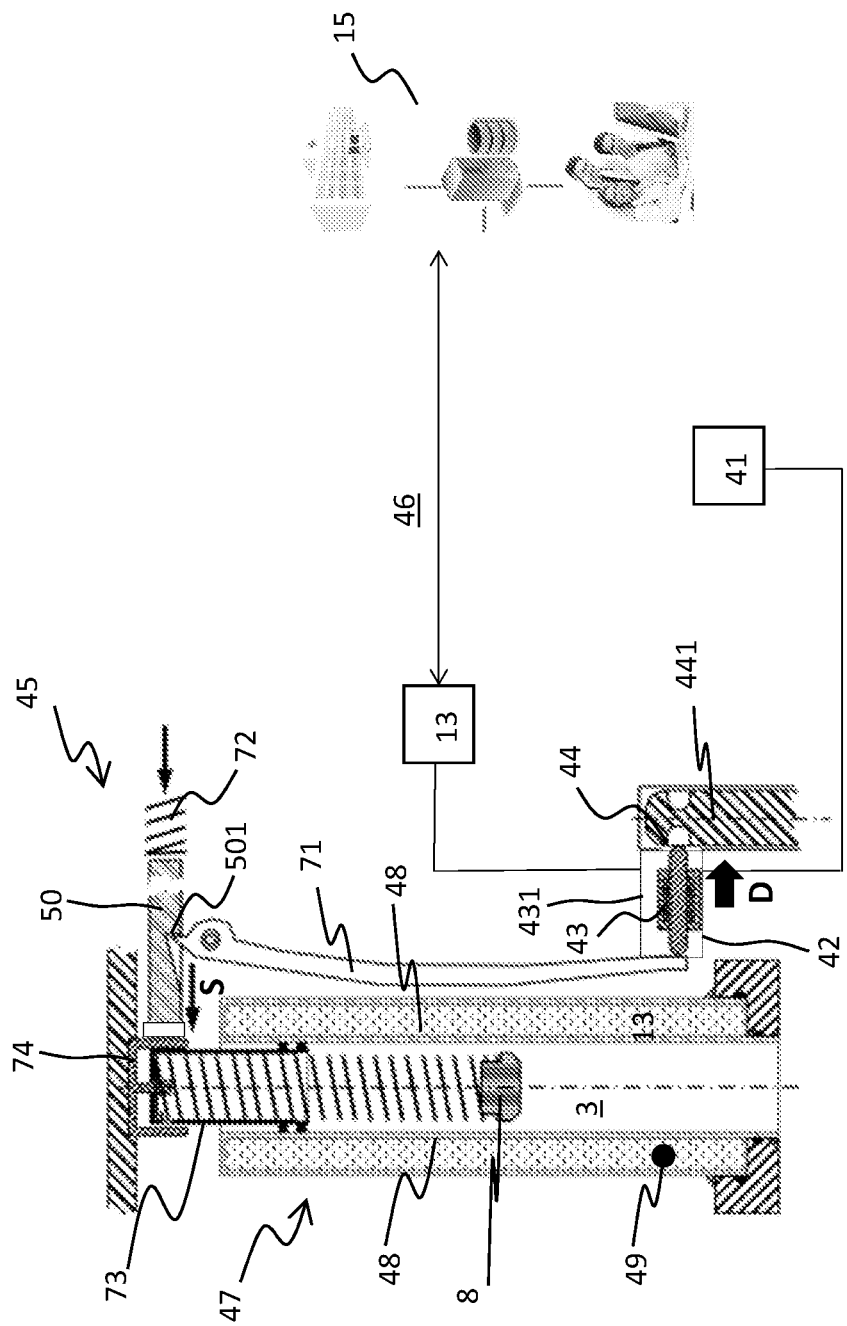
FIGS. 15-17 show an exemplary embodiment of a destruction system of the medicament dispenser.

In some embodiments, with reference to next FIG. 15, medicament dispenser may comprise a destruction system 45 of the medicaments contained therein.

In some embodiments, destruction system 45 may be activated by control unit 13 upon reception of a service destruction order 46 from the remote server 15.

In some scenarios, doctor/medical stuff may decide to remotely neutralize the medicaments contained in the medical dispenser, if there is a risk that user may be in some way capable of accessing its internal storage for uncontrolled and hence dangerous intake.

Destruction system 45 comprises a reservoir 47 disposed within the internal storage 3, which has internal frangible walls 48 and contains a medicament-neutralizing agent 49.

Destruction system 45 further includes a puncher element 50 which is configured to break, when activated, the internal frangible walls 48 and release the medicament-neutralizing agent 49 within the internal storage 3, thus coming into contact with the medicaments and neutralizing the active principle.

In this exemplary embodiment, puncher element 50 is kept in balance between two opposed forces: a spring 72 which forces the puncher 50 in the direction of arrow S and a an opposed force exerted by a crank 71 which mechanically engages a step 501 of puncher 50 in correspondence of its upper end. Lower end of crank 71 abuts to a movable pin 43 of an electro-mechanical switch 42. When the pin 43 is activated, it irreversibly slides along direction of arrow D. The slide of pin 43 causes crank 71 to remove engagement with puncher 50 and cease the force exerted to the latter to keep it in balance against spring force 72. This causes a sudden slide of the puncher element 50 along direction of arrow S towards an impulse transmission element 73, which is connected to the main body of the dispenser by a support 74. The impulse is then transmitted towards the internal frangible walls 48 of reservoir 47, thus causing release of neutralizing agent 49 in the storage and consequent destruction of medicaments.

More in the specific, slidable pin 43 is constantly subject to a resilient force and it is maintained in the position depicted in the figure, by an electric circuit, schematically indicated with numeral 41, which exerts a force opposed to the resilient one and keeps it in balance. Upon reception of service destruction order 46, control unit 13 disables the electric circuit 41. In this way, resilient force determines the slide of pin 43 along direction of arrow D and thus the sudden movement of puncher 50 in the direction of arrow S.

In some exemplary embodiments, as depicted in the figure, electro-magnetic switch 431 may be advantageously arranged between the lower end of crank 71 and the portion 441 of cover 29 in correspondence of its groove 44. In this way, service destruction order 46 causes both its projection into the receiving groove 44 for permanently preventing removal of the cover 29, and the release of the puncher 50 for breaking the reservoir frangible walls 48.

This arrangement may be particularly advantageous in case neutralizing agent 49 is harmful for the user. In this case, in addition to medicaments destruction, it is ensured that internal storage is still not accessible by the user to prevent user come into contact with neutralizing agent 49.

In this exemplary embodiment, internal walls 48 of reservoir 47 define the internal storage 3 where the medicaments are accommodated and the reservoir 47 is therefore located around the storage 3. However, other embodiments may be considered where, for example, reservoir is entirely contained within the internal storage and arranged such that its breakage causes release of agent 49 therein.

In this exemplary embodiment, reservoir internal walls 48 may be made of a material which may be transparent, and which is fragile under certain mechanical stress conditions, and which can be glass, such as normal glass, as silicate glass or similar, composed of approximately 75% silicon dioxide ($SiO_2$), sodium oxide ($Na_2O$), calcium oxide (CaO), and additives, as well as thermal treated glass to have defined physical mechanical behavior upon specific mechanical stress, such as breaking and fragmenting according to specific pattern, etc. The material of internal walls 48 can be made of other types of glass, such as fluoride glasses, aluminosilicates, phosphate glasses, borate glasses, and chalcogenide glasses, glass-ceramics, as well as it can be made of polymeric materials, or compounds, which have similar physical properties, namely a hard material that is normally breakable when submitted to mechanical stress within the range of force needed to break the material according to its specific material characteristics and its specific design in terms of its surface.

Figure 16:
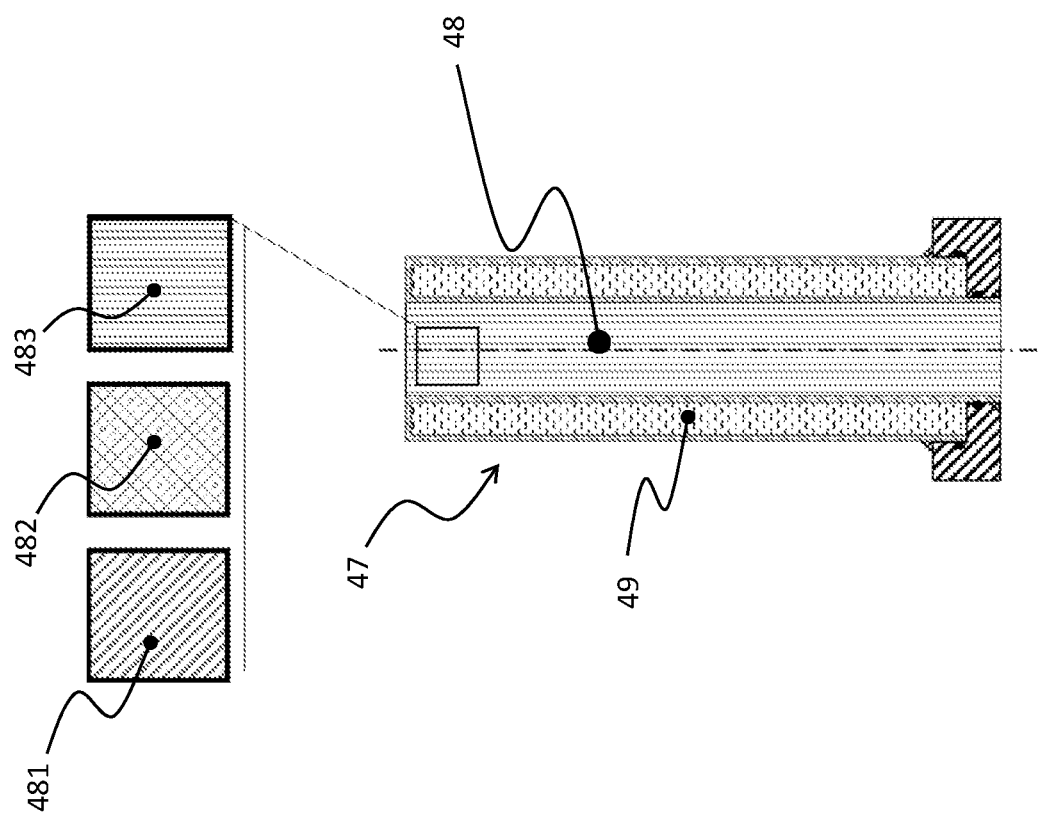

With reference to next FIG. 16, internal reservoir walls 48 may include pre-cut lines in one or more directions in order to facilitate breakage of the material. For example, internal walls 48 may be provided with diagonal/helical lines 481, or crossing/diamond lines 482, or longitudinal lines 483.

Figure 17:
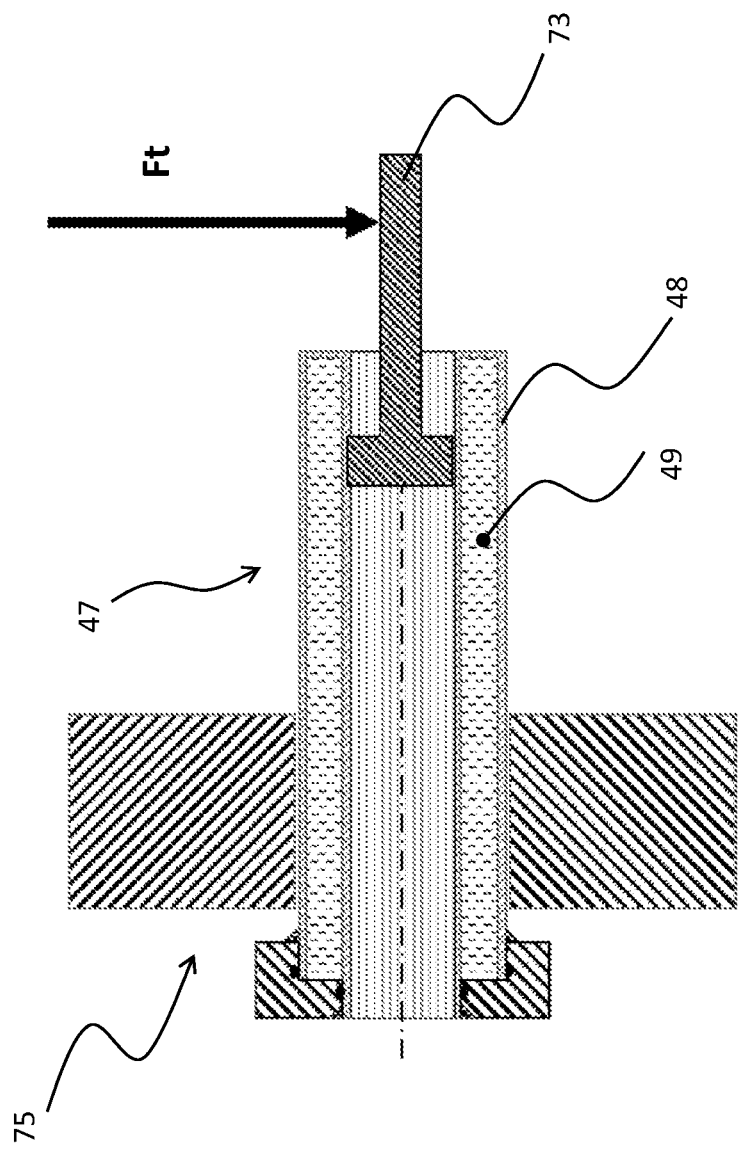

Calculation of necessary force $F_t$ to be applied by puncher 50 to the impulse transmission element 73 may be measured using a standard testing apparatus 75, as illustrated in FIG. 17. Such force may be comprised in the range 6 N to 120 N, preferably from 15 to 50 N.

Figure 18:
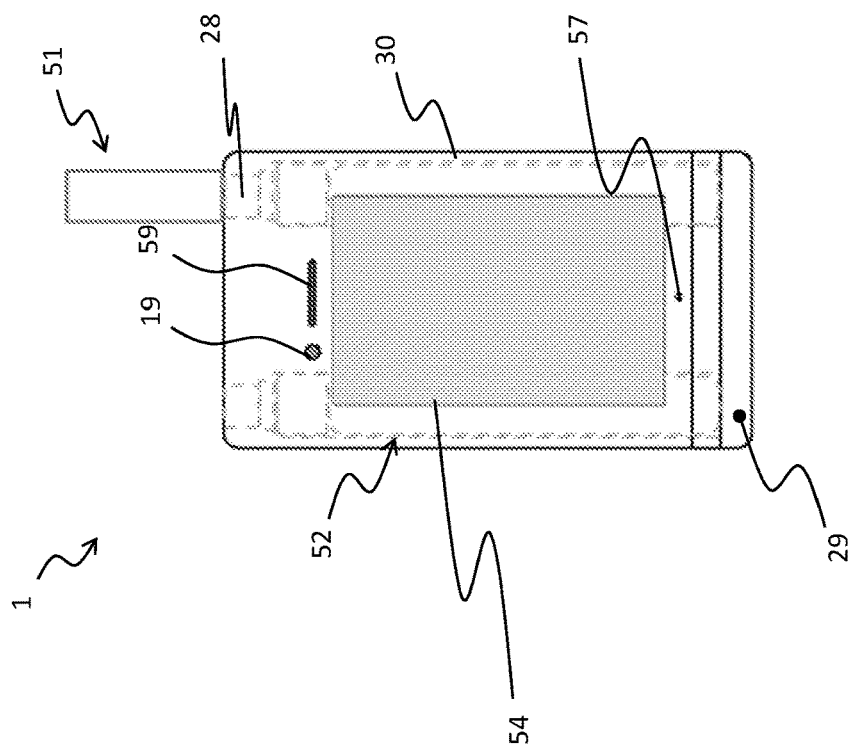
Figure 18:
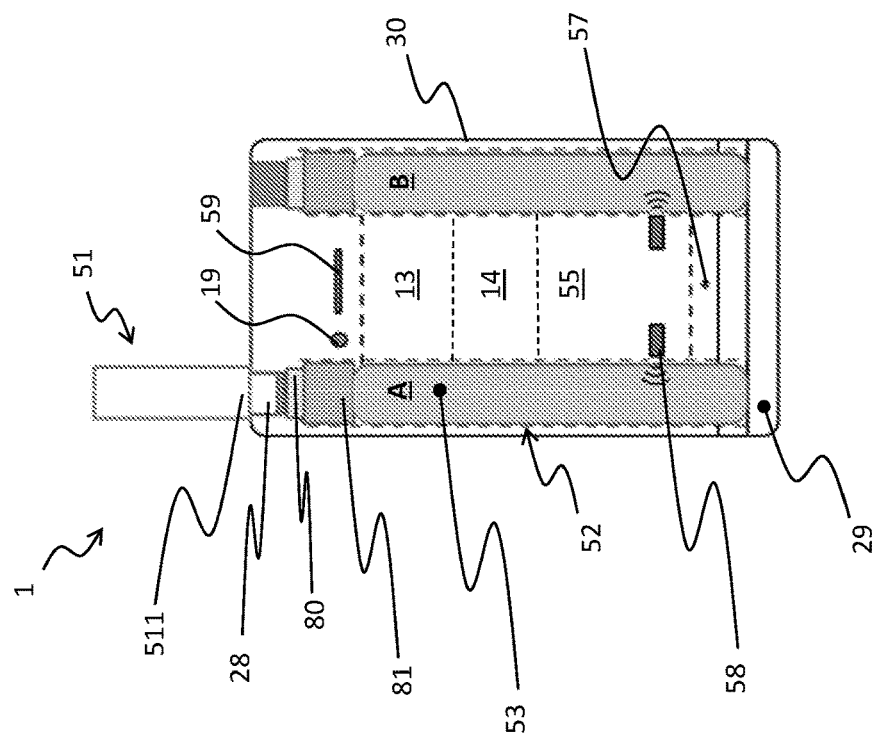

With now reference to next FIG. 18, it is shown a further exemplary embodiment of the medicament dispenser 1 according to the invention. In this embodiment, the internal storage of the medicament dispenser, where medicament is stored, may accommodate a canister 52 which is adapted to store the medicament in a form such to be delivered to the user as an inhalable aerosol 53. The main components of dispenser 1 are the same as the one already detailed, so the detailed description will be omitted.

In this embodiment, medicament dispenser 1 is couplable to an inhaler, 51, which may be disposable or re-usable. To this aim, inhaler 51 includes an end portion 511 which is configured to be coupled to an upper component 28 of canister 52 for inhaling the medicament in form of the aerosol 53.

In this exemplary embodiment, medicament dispenser 1 includes two independent canisters A and B, each one carrying a different type of medicament. However, it will be appreciated that medicament dispenser 1 may comprise canisters 52 in any number, for storing the same type of medicament 53 or, differently, each canister 52 may include a different type of medicament, depending on the specific user's dispensing protocol.

In this embodiment, similarly to previously described embodiment, internal storages of medicament dispenser 1 may be charged or refilled via the cover 29 with canisters 52, In this embodiment, the usage of two different types of medicaments advantageously enables the controlled delivery of each medicament independently, or with correlated delivery, according to the dispensing protocol, and in such cases the geometrical cross-section of the internal storages and related canisters' embodiments may differ between them to enable easier and safer recognition.

In this embodiment, medicament dispenser 1 may have aerosol producing components, such as a homogenizer chamber 81 which may have specific cross-section for the purpose of better homogenization of the aerosol, including axially converging towards the outlet, like conical funnel, or converging and diverging, like converging conical and diverging conical towards the outlet of the inhaler 51. When the inhaler 51 is coupled with the medicament dispenser 1 via the upper component 28 (threaded, bayonet, or other) the inhaler cross-section may extend the feature and effect of homogenization chamber.

Figure 19:
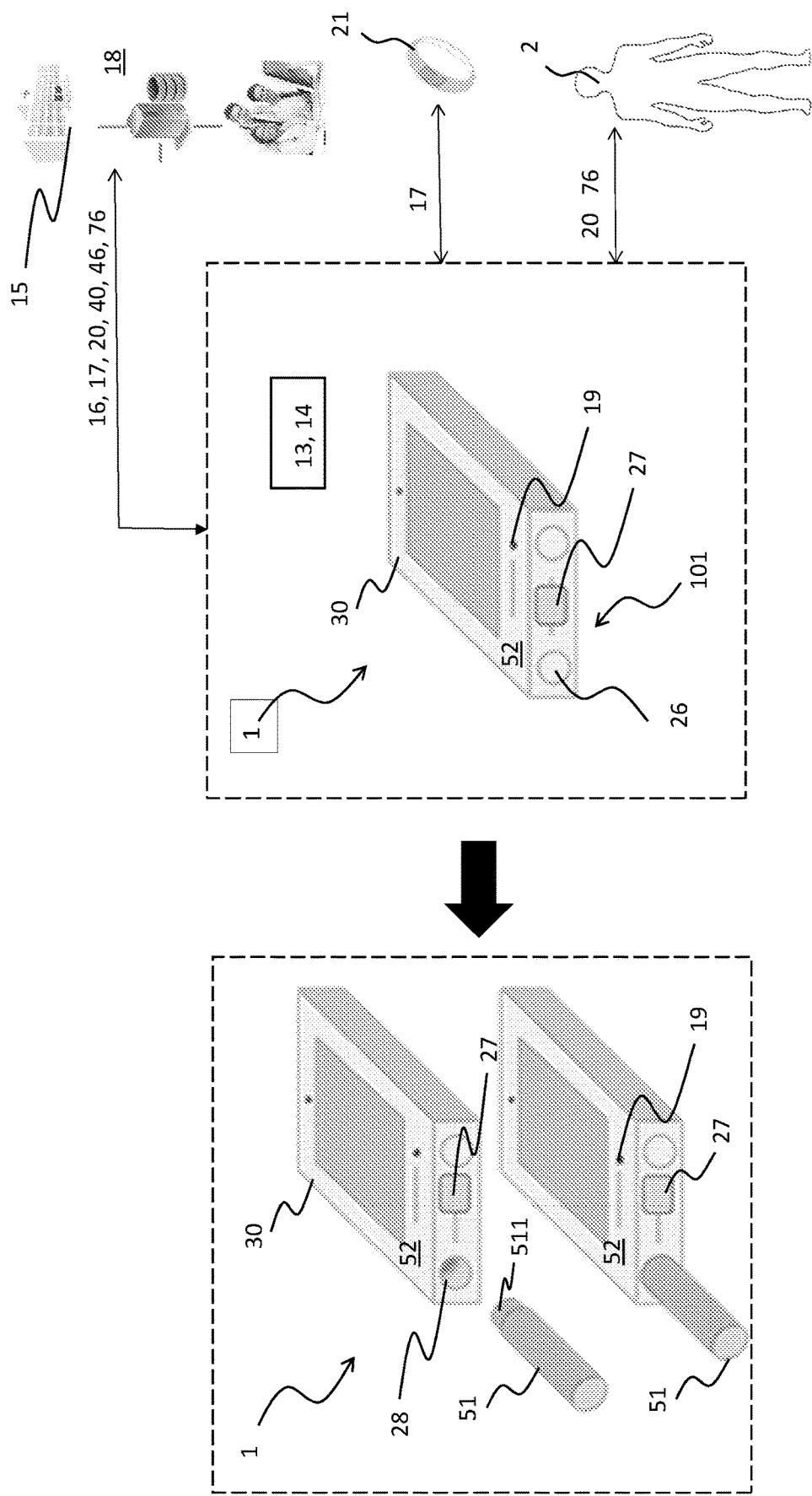

With reference to next FIG. 19, it is described an exemplary usage of medicament dispenser 1 according to this embodiment. User 2 accesses the medicament dispenser 1 and authenticates his identity by input of his/her user authentication data 76. Health data 17 collected by the wearable device 21 may also be input into the medicament dispenser 1. Control unit 13 collects user authentication data 76 and user health data 17 and exchange such piece of information through communication module 14 with the remote server 15. Remote server 15 elaborates the information and, based on the dispensing protocol established for the authenticated user 2, inputs control delivery data 16. It will be appreciated that, based on current user's health data 17, dispensing protocol 18 may be varied, thus affecting the delivery control data 16. As an example, if health data 17 is considered abnormal, medicament delivery may be interrupted.

In this embodiment, dispensing unit 101 comprises a movable shutter 26, movable by the user 2 through a slidable lever 27, to access internal storage which contains canisters 52 provided with a medicament in a form such to be delivered as inhalable aerosol for medicament intake.

If all conditions are met and control delivery data 16 contains instructions for a medicament delivery, then control unit 13 enables opening of shutter 26 with slidable lever 27. Once shutter 26 has been opened, user may connect the inhaler 51 to the medicament dispenser 1 by coupling end portion 511 of the inhaler 51 to the upper component 28 of the dispenser 1, as clearly shown in the figure. In this configuration, medicament dispenser 1 is ready to be used and deliver predefined doses of inhalable gas to the user in accordance to the predefined dispensing protocol.

In such cases of medicaments (for example opioids) in aerosol forms, those aerosols may be produced by thermal aerosolization based on electrical resistive heat or induction heating systems, or nozzles spraying or dispersing liquids from pressurized containers, pumps or micro-pumps, as well as aerosols produced using ultrasound systems. In any case of the use of the aerosols, for example opioids based pain relief medicine, medicament dispenser 1 is advantageously provided with metering capabilities to assure the delivery of a specified dose, such as using metered pump aerosolizing devices which deliver a fixed volume. In the case of the medicament dispenser using thermal aerosolization systems, such as electrical resistive heat or induction heating systems using canisters/cartridges with liquid forms of medicine for the purpose of thermal aerosolization, a reliable way of metering the dose and control the delivery may be obtained by controlling the time of activation of the heating unit, and therefore knowing the volume of liquid consumed in such activation and therefore the aerosol produced and inhaled by the user. In this way, control unit 13 of dispenser 1 controls the delivery and consumption of the medicament, and the effective consumption, in accordance to the dispensing protocol 18. As already mentioned, general condition of user 2 and the effects of the specific consumption can be monitored remotely by the doctor/medical stuff via heath data 17, including via pupilometry, using camera 19 of the medicament dispenser 1 to obtain data related to the status of the pupil of the user before and after the intake of the medicament.

Figure 20:
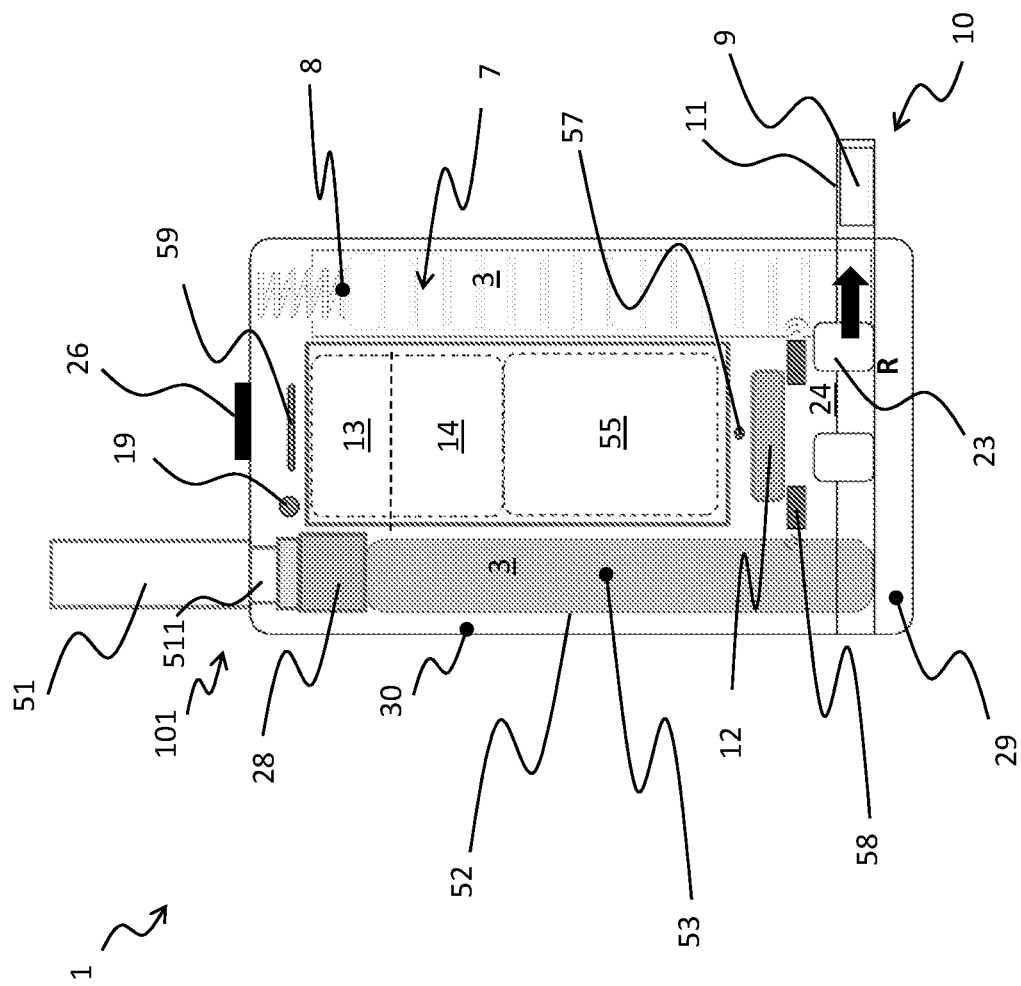

With reference to next FIG. 20, it is shown yet a further embodiment of medicament dispenser 1. In this example, medicament dispenser 1 includes two internal storages 3, wherein one storage 3 accommodates a canister for medicament delivery in the form of inhalable aerosol, while the other storage 3 is configured to store tablets 9 in the form of a pile 7.

This embodiment enables the use of controlled delivery of tablets 9 for a specific medicament, as well as the controlled delivery of a medicament to be inhaled via aerosol, such as opioids. This embodiment is therefore very advantageous in cases of users suffering debilitating dyspnea and sever bronchogenic, where opioids administered in aerosol form can be effective pain relief, including users with lung cancer, strongly supporting those patients in cases of gradual deterioration in quality of life.

Each storage of medicament dispenser 1 according to this embodiment operates as previously described, so a further description of such hybrid embodiment of the medicament dispenser will be omitted.

Broadly speaking, medicament dispenser 1 according to the invention may comprise any number of internal storages for storing medicaments, wherein each medicament stored in the respective storage may be provided in any forms and/or types.

Figure 21:
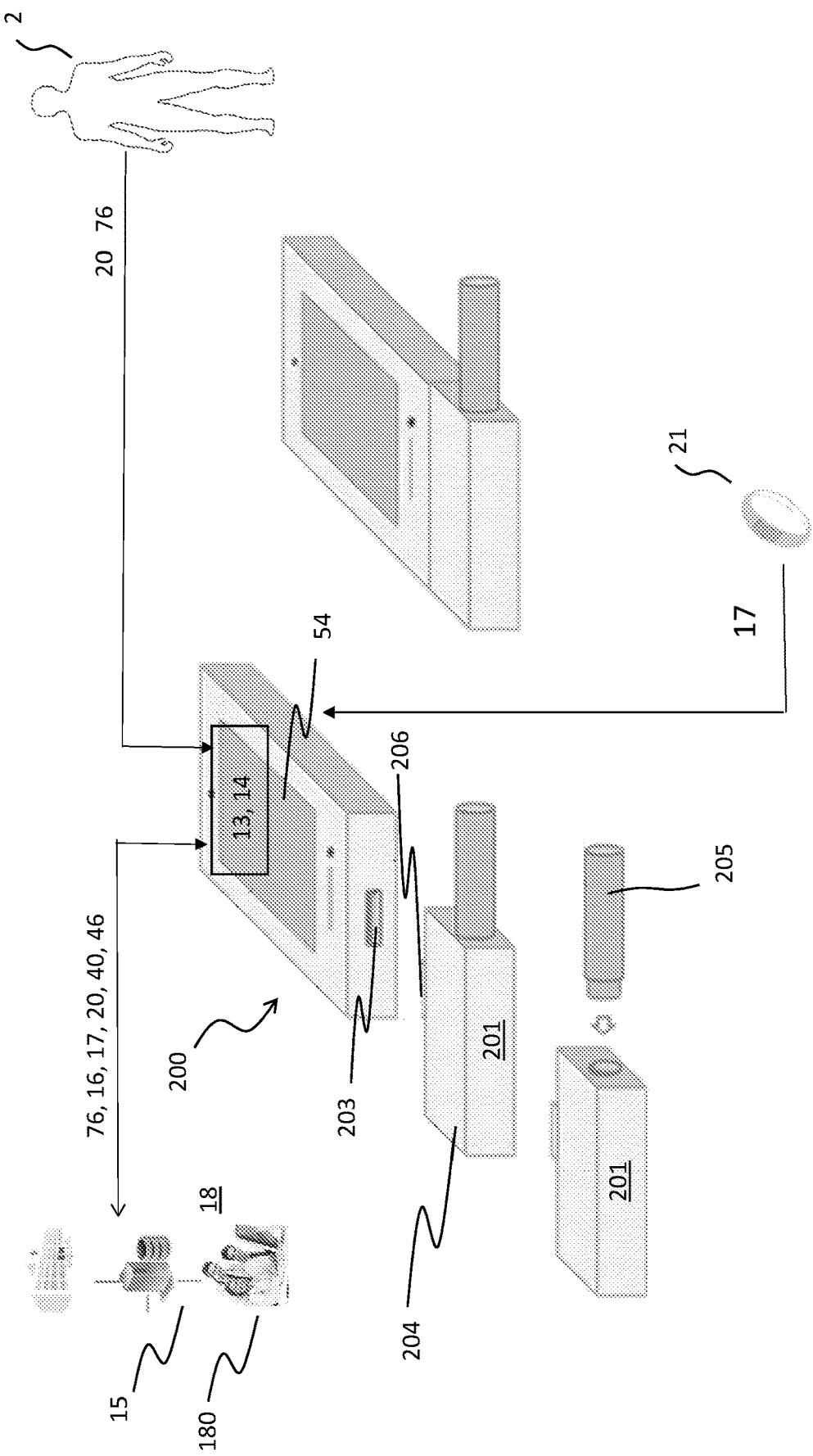

Making now reference to FIG. 21, it is depicted yet a further embodiment of the medicament dispenser according to the invention, indicated with numeral reference 200. In this example, medicament dispenser 200 comprises a connector 203 for connecting the medicament dispenser 200 to an external storage 204, in turn adapted to internally store a medicament, indicated with numeral 201 in the figure. Medicament dispenser 200 further includes a control unit 13 which comprises a user recognition unit adapted to collect user authentication data 76 and a communication module 14, configured to send/receive the user authentication data 76 and a delivery control data 16 to/from a remote server 15, wherein the delivery control data 16 is associated to a predefined dispensing protocol 18 of the user 2.

It will be appreciated that the main difference of this embodiment with previous embodiments above described resides in the fact that medicament storage 204 is no longer an inner portion of the dispenser 200, but it is a detachable external component. In this case, control unit 13 is configured to enable/disable delivery of medicament 201 from the external storage 204 to the user 2, when connected to the dispenser 200, based on the user authentication data 76 and the delivery control data 16.

In this example, connector 203 is a female slot adapted to engage with a male component 206 of the external storage 204 enabling stable and robust physical and electrical connection between the dispenser 200 and an external storage 204 which carries the medicament 201.

In this example, external storage 204 may be configured for aerosol production and delivery trough a mouthpiece 205, External storage 204 may comprise an independent power source, such us at least one battery, and electronics (not shown) interfacing with the electronics, namely the control unit 13, of the medicament dispenser 200 (namely control unit 13) and/or the auxiliary device 21.

Alternatively, external storage 204 may use the electronics and power supply of medicament dispenser 200.

In some embodiments, operative functions may be displayed on display 54, which may also have touch-screen capabilities.

The present invention has hereto been described with reference to a preferred embodiment. It is to be understood that there may be other embodiments afferent to the same inventive concept, and all falling within the scope of protection of the claims below.

The invention claimed is:

1. A medicament dispenser for delivering a medicament to a user, the medicament dispenser comprising:
one or more internal storages for storing one or more medicaments;
a dispensing unit configured to access said one or more internal storages and dispense the medicament based on a predefined dispensing protocol;
a control unit comprising a user recognition unit, adapted to collect user authentication data, and a communication module configured to send and receive said user authentication data and a delivery control data associated with said predefined dispensing protocol to and from a remote server;
a destruction system for destruction of the medicaments, the destruction system comprising a reservoir disposed within the one or more internal storages and an electro-mechanical switch, the reservoir having frangible walls and containing a medicament-neutralizing agent, the reservoir being arranged within the one or more internal storages such that upon breakage of the frangible walls, the medicament-neutralizing agent is released within the one or more internal storages; and
a puncher element configured to break, when activated, the frangible walls, wherein the electro-mechanical switch includes a component having a slidable pin such that, when activated, the slide of the pin triggers a release of the puncher element for breaking the reservoir walls;
wherein said control unit is configured to enable or disable said dispensing unit based on said user authentication data and said delivery control data.

2. The medicament dispenser according to claim 1, wherein said destruction system is activable by said control unit to destroy the medicaments upon reception of a service destruction order from the remote server.

3. The medicament dispenser according to claim 1, wherein said destruction system is associated with an internal electric circuit configured to detect a local attempt of forcing the medicament dispenser to access the one or more internal storages, wherein said destruction system is activated to destroy the medicaments if such attempt is detected.

4. A medicament dispenser for delivering a medicament to a user, the medicament dispenser comprising:
one or more internal storages for storing one or more medicaments;
a dispensing unit configured to access said one or more internal storages and dispense the medicament based on a predefined dispensing protocol;
a control unit comprising a user recognition unit, adapted to collect user authentication data, and a communication module configured to send and receive said user authentication data and a delivery control data associated with said predefined dispensing protocol to and from a remote server;

a cover for accessing the one or more internal storages, said cover being removably connected to a main body of the medicament dispenser by a locking/unlocking means;

a safety clamping mechanism configured to irreversibly prevent unlocking of said cover, the safety clamping mechanism comprising an electro-mechanical switch including a component having a slidable pin;

a destruction system for destruction of the medicaments, the destruction system comprising a reservoir disposed within the one or more internal storages, the reservoir having frangible walls and containing a medicament-neutralizing agent, the reservoir being arranged within the one or more internal storages such that upon breakage of the frangible walls, the medicament-neutralizing agent is released within the one or more internal storages, wherein said electro-mechanical switch is arranged such that sliding of the slidable pin causes both projection of the slidable pin into a receiving groove of the cover for preventing removal of the cover and release of a puncher element for breaking the reservoir walls;

wherein said control unit is configured to enable or disable said dispensing unit based on said user authentication data and said delivery control data.

5. The medicament dispenser according to claim 4, wherein said destruction system is activable by said control unit to destroy the medicaments upon reception of a service destruction order from the remote server.

6. The medicament dispenser according to claim 4, wherein said destruction system is associated with an internal electric circuit configured to detect a local attempt of forcing the medicament dispenser to access the one or more internal storages, wherein said destruction system is activated to destroy the medicaments if such attempt is detected.

* * * * *